United States Patent [19]
Rexroth et al.

[11] Patent Number: 4,739,759
[45] Date of Patent: Apr. 26, 1988

[54] MICROPROCESSOR CONTROLLED ELECTROSURGICAL GENERATOR

[75] Inventors: Frederick W. Rexroth, Dunedin; Gary R. Hoss, Largo, both of Fla.

[73] Assignee: Concept, Inc., Clearwater, Fla.

[21] Appl. No.: 705,922

[22] Filed: Feb. 26, 1985

[51] Int. Cl.$^4$ ............................................. A61B 17/39
[52] U.S. Cl. ........................... 128/303.14; 128/303.17
[58] Field of Search ............ 128/303.1, 303.11–303.15, 128/303.17, 804; 330/137, 207 A

[56] References Cited

U.S. PATENT DOCUMENTS

| | | | |
|---|---|---|---|
| 2,498,659 | 2/1950 | DeRosa | 330/137 |
| 3,058,470 | 10/1962 | Seeliger et al. | 128/303.14 |
| 3,112,365 | 11/1963 | Kihara | 330/207 A |
| 3,702,940 | 12/1972 | Stewart | 128/303.1 |
| 3,964,487 | 6/1976 | Judson | 128/303.14 |
| 4,024,467 | 5/1977 | Andrews et al. | 128/303.14 |
| 4,071,028 | 1/1978 | Perkins | 128/303.14 |
| 4,126,137 | 11/1978 | Archibald | 128/303.14 |
| 4,378,801 | 4/1983 | Oosten | 128/303.14 |
| 4,438,766 | 3/1984 | Bowers | 128/303.14 |
| 4,569,345 | 2/1986 | Manes | 128/303.14 |
| 4,574,801 | 3/1986 | Manes | 128/303.14 |
| 4,590,934 | 5/1986 | Malis et al. | 128/303.17 |
| 4,617,927 | 10/1986 | Manes | 128/303.14 |

FOREIGN PATENT DOCUMENTS

| | | | |
|---|---|---|---|
| 136855 | 4/1985 | European Pat. Off. | 128/303.13 |
| 2,910,196 | 9/1980 | Fed. Rep. of Germany | 128/303.13 |
| 3420339 | 1/1985 | Fed. Rep. of Germany | 128/303.13 |
| 2154881 | 9/1985 | United Kingdom | 128/303.17 |

*Primary Examiner*—Lee S. Cohen
*Assistant Examiner*—David Shay
*Attorney, Agent, or Firm*—Epstein & Edell

[57] ABSTRACT

A microprocessor controlled electrosurgical generator provides plural ground-isolated and mutually isolated monopolar r-f cutting signals for respective surgical pencils to permit plural surgeons to use the same generator while maintaining independent control over output power and mode selection. A bipolar output signal is also isolated from ground and from the monopolar signals so that the removal of the dispersive patient return pad is not required when changing between monopolar and bipolar operation. Adjustment of the r-f cutting signal power level is effected by providing an adjustable d.c. bias level for an output amplifier. The d.c. bias level is derived from an a.c. control signal which is duty-cycle modulated in accordance with selected r-f power level settings. Digital phase control is employed to change the control signal duty cycle by subdividing the control signal cycle into precise count intervals and triggering a gate to pass the control signal through a rectifier to a filter for only the selected number of count intervals in each cycle as determined by a pre-settable counter. Negative feedback of the cutting signal to the input terminal of the output amplifier provides system stability during open circuit operation.

20 Claims, 16 Drawing Sheets

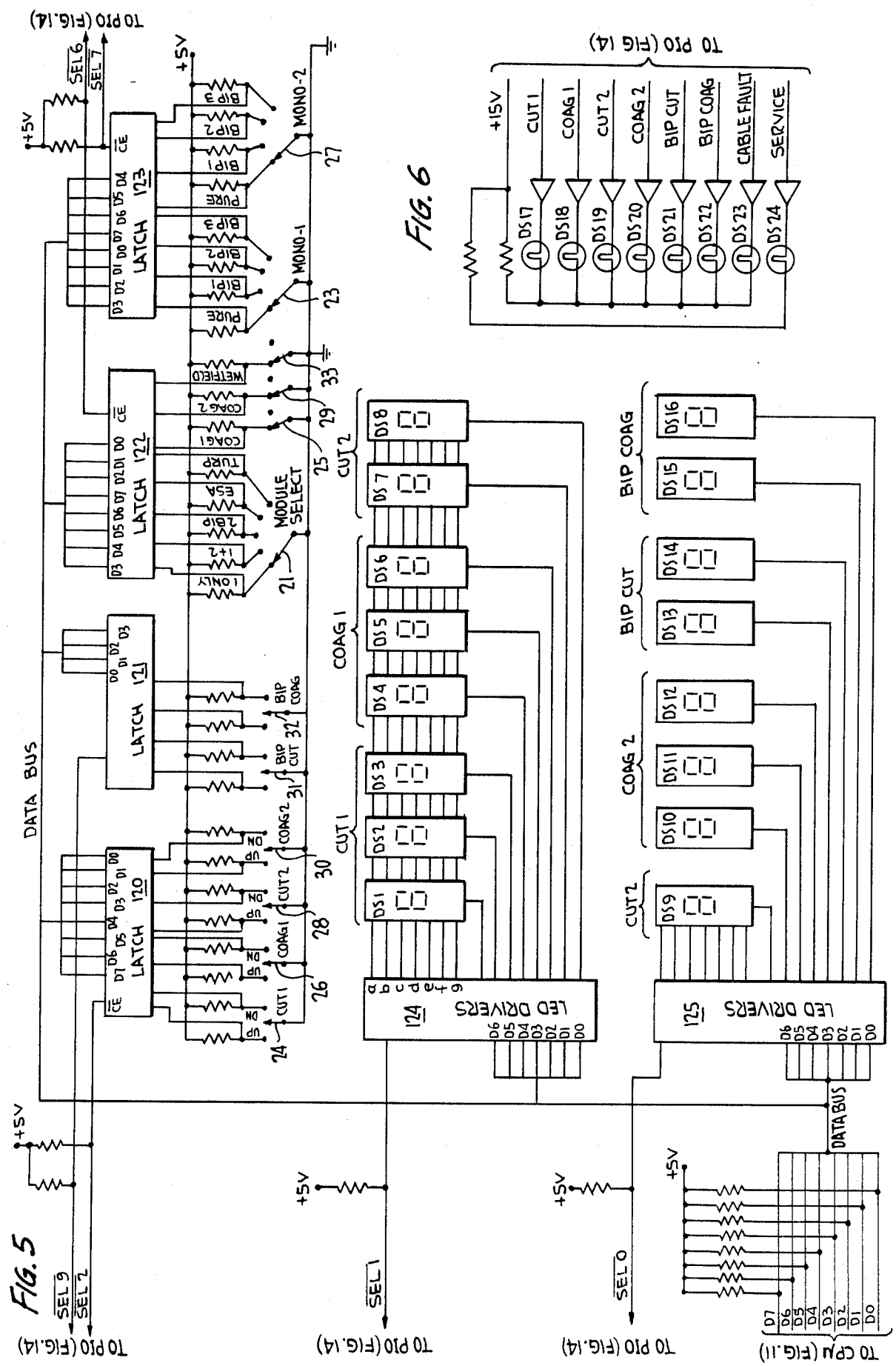

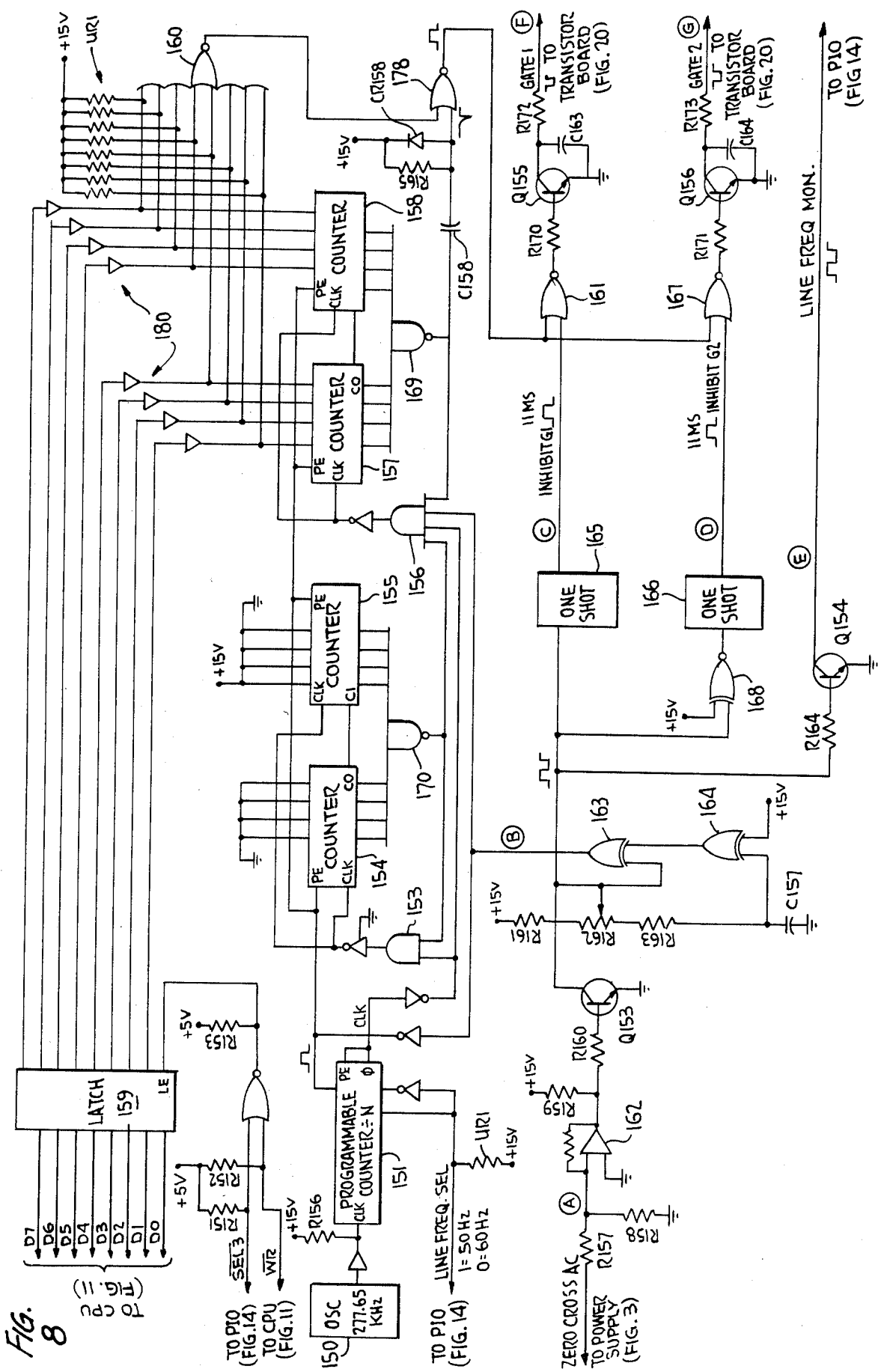

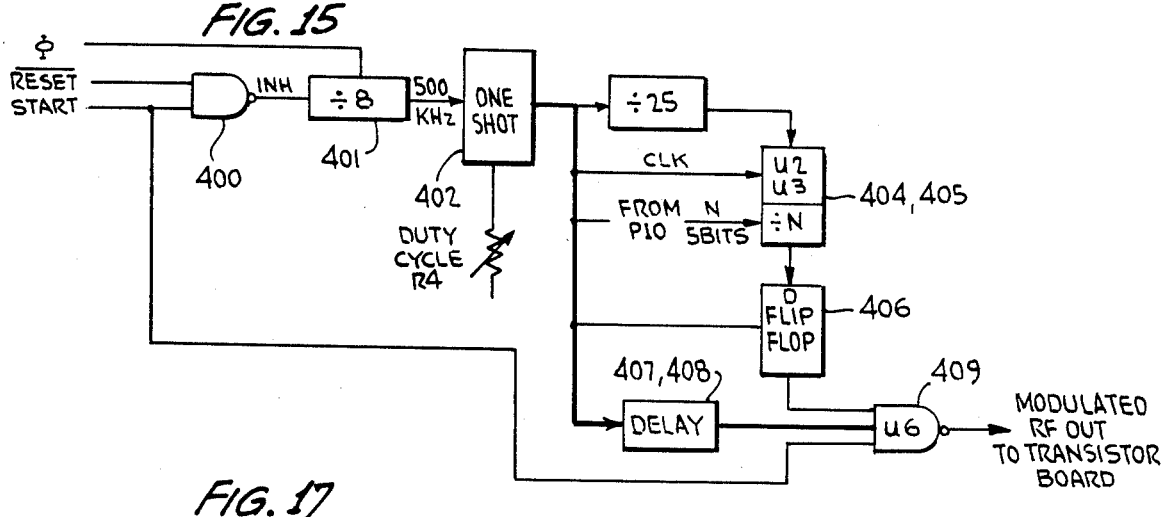
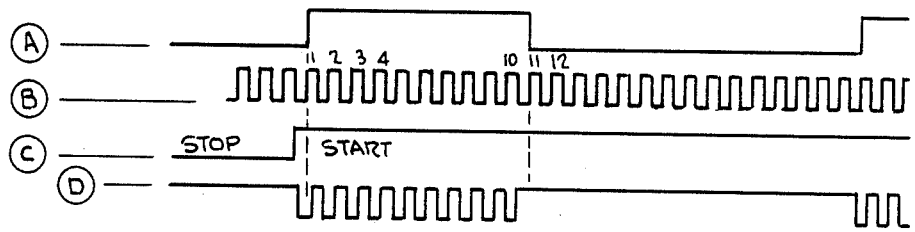
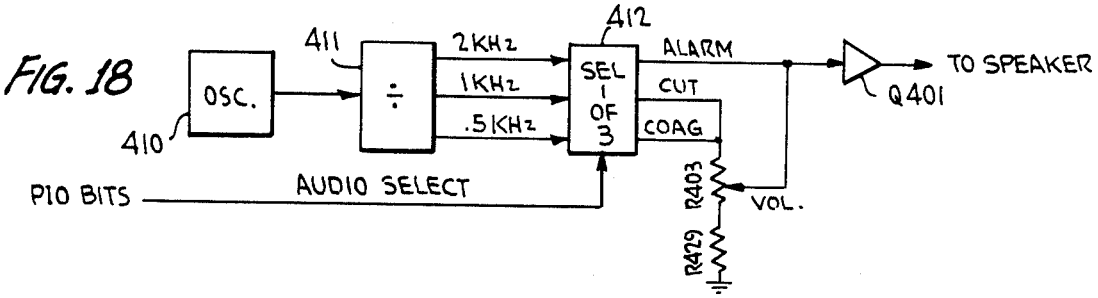
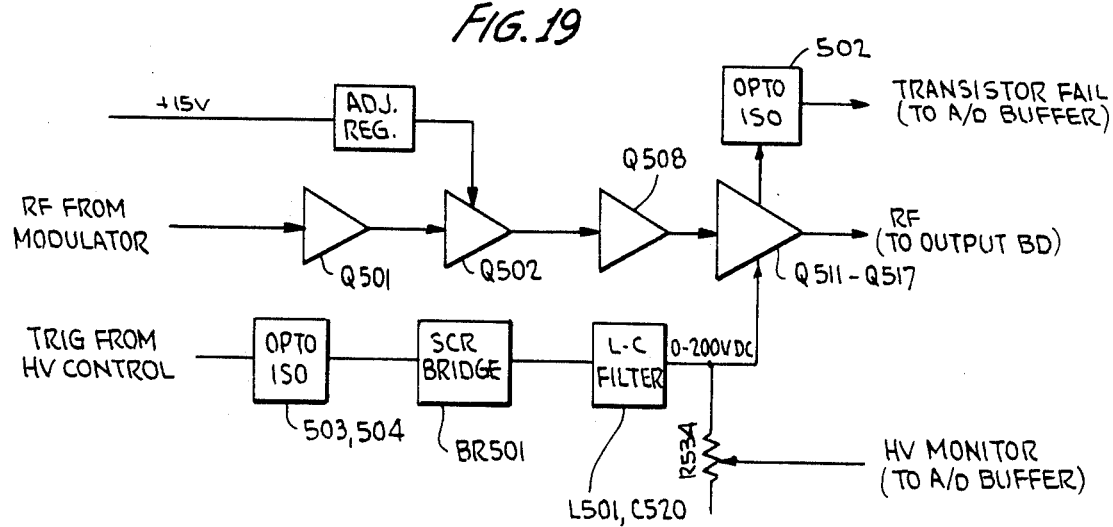

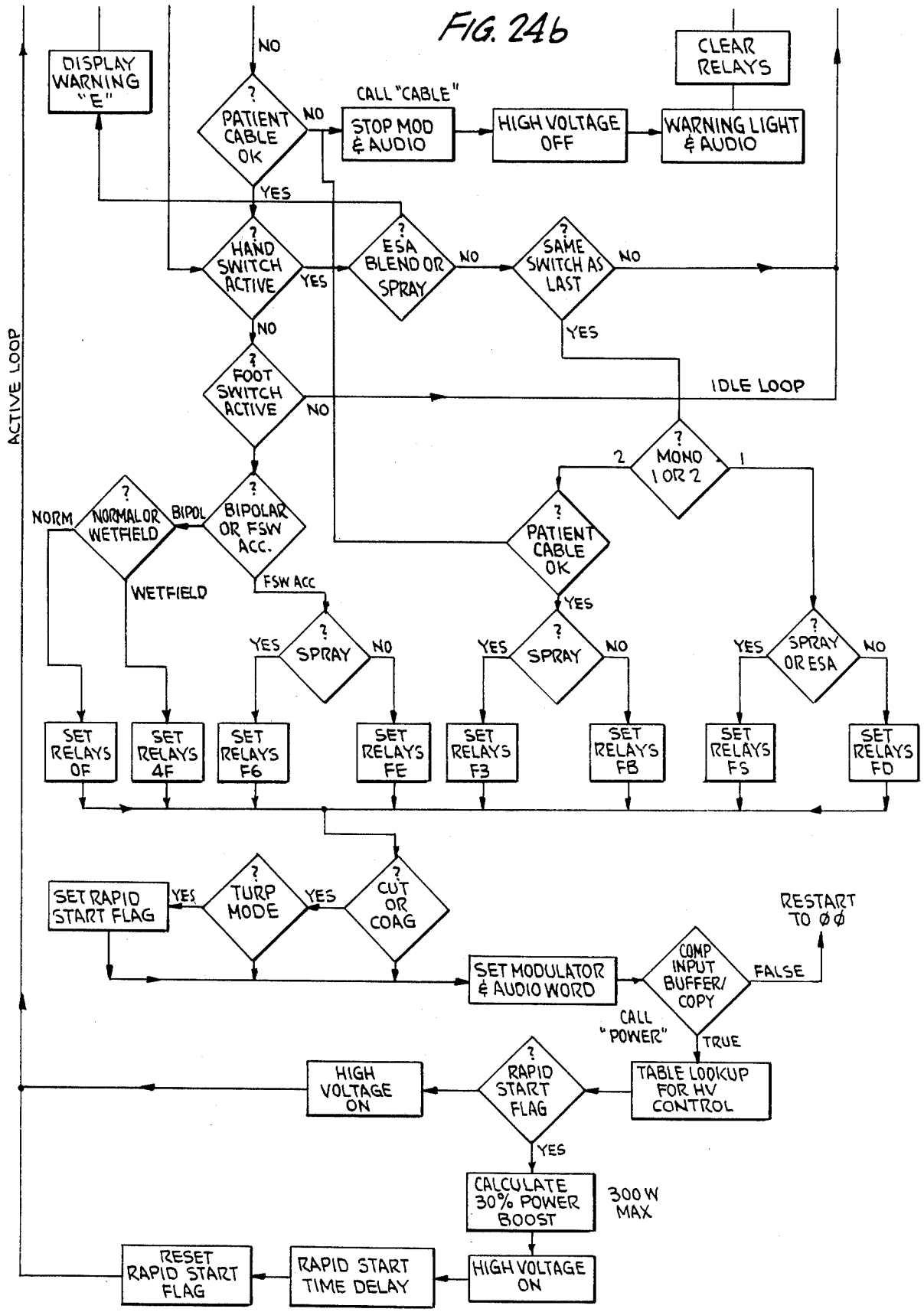

MICROPROCESSOR CONTROLLED ELECTROSURGICAL GENERATOR

BACKGROUND OF THE INVENTION

1. Technical Field

The present invention relates to electrosurgical generators and, more particularly, to electrosurgical generators which are microprocessor-controlled to permit use by more than one surgeon from a single unit and to provide accurate adjustable control of the cutting signal power level.

2. Discussion of the Prior Art

Electrosurgical generators of the type with which the present invention is concerned are described and illustrated in the following U.S. Pat. Nos.: 4,038,984 (Sittner); 4,188,927 (Harris); 4,318,409 (Oosten); 4,378,801 (Oosten); 4,429,694 (McGreevy); 4,438,766 (Bowers); and 4,473,075 (Rexroth). To the extent that such patents provide a general background and understanding of the electrosurgical generator field and technology, the disclosures in those patents are expressly incorporated herein, in the entireties, by this reference.

Electrosurgical generators are capable of operating in four primary surgical modes, namely: dessication; fulguration; cutting; and cutting with hemostasis. Dessication and fulguration are considered parts of a coagulation mode. The level and waveform of the r-f power of voltage applied to the surgical site differs for the various modes.

The signal for performing electrosurgical operations is typically generated by a radio-frequency (r-f) generator connected to a power amplifier. The output signal from the power amplifier is delivered to the tissue mass by means of two electrodes. Monopolar surgical operations are performed by means of an active electrode which introduces the r-f current into the tissue mass. A dispersive patient return pad constitutes the second electrode. The active electrode typically has a small cross-section to concentrate the power and to limit the surgical effect to a small controlled area. The return path from the tissue mass to the generator is provided by the dispersive pad which has a large area to prevent electrosurgical effects from taking place at the current return location. Alternatively, a pair of active electrodes may be employed in a bipolar mode in which the electrosurgical effects are confined to the tissue located between the two electrodes.

In the cutting mode, the cutting signal is a high frequency signal which serves to cut through tissue when the signal is applied to the patient. The electrode is used to apply the electrical energy to defined and concentrated points at the surgical site. Cutting is accomplished by the concentrated application of r-f energy which effectively destroys body cells directly beneath the electrosurgical electrodes. Coagulation signals are intended to produce coagulation by shrinking vessel walls. Typically, such coagulation signals are pulses of energy having a damped sinusoidal waveform. Coagulation signals may be viewed as causing cell dehydration to produce coagulation rather than destroying cells in the fashion of cutting signals. Blended signals are formed by combining the cutting and coagulation signals, and are useful for accomplishing cutting and coagulation simultaneously. Alternating periods of each signal may be employed to form the blended signal.

It is desirable to provide electrosurgical generators with power adjustments so that surgeons can adjust the power level as necessary in each of the operating modes. Power adjustability is available in prior art electrosurgical generators; however, the adjustment is neither sufficiently accurate nor sufficiently precise for many delicate surgical procedures.

Moreover, prior art electrosurgical generators cannot be employed by two or more surgeons, using respective surgical pencils, with independent mode and power control for each pencil.

Another problem with prior electrosurgical generators concerns the need for removing the dispersive patient return pad when changing from monopolar to bipolar operation, and the replacing of the pad when returning to monopolar operation. If the pad is not removed for bipolar operation, the cutting signal is at least partially diverted from its path between the two bipolar electrodes to unwanted paths from either or both electrodes to the pad.

OBJECTS AND SUMMARY OF THE INVENTION

It is therefore an object of the present invention to provide an electrosurgical generator in which the power level of the cutting signal is accurately selected and precisely controlled in each of the generator operating modes.

It is another object of the present invention to provide an electrosurgical generator which can be used by more than one surgeon while maintaining separate mode and power control for each surgeon.

Another object of the present invention is to provide an electrosurgical generator capable of changing between monopolar and bipolar operation without removal of the dispersive patient return pad employed during monopolar operation.

It is still another object of the present invention to provide a microprocessor-controlled electrosurgical generator capable of monitoring and controlling the operation of plural surgical pencils.

In accordance with the present invention, an electrosurgical generator is provided with a plurality of accessory connectors for connection to respective surgical pencils. The r-f signals applied to each accessory connector are mutually isolated and isolated from ground so that none of the signals is affected by the output circuitry of the others. In this manner, the dispersive patient return pad is effectively removed from the circuit automatically during bipolar operation and is not part of the signal return path to the generator.

Each accessory includes an independent power level adjustment with a digital display. The selected power level determines the value of a number which is preset into a counter at the start of each half-cycle of an a.c. control signal. The counter effectively subdivides the control signal half-cycle into multiple precisely defined sub-intervals. Trigger pulses are generated at a trigger time which varies within the half-cycle in accordance with the pre-set number in the counter. The trigger pulses are employed to trigger gates in a full wave rectifier to pass only portions of the control signal half-cycle occuring subsequent to the trigger pulse. The duty cycle of the control signal is thereby effectively modulated as a function of the pre-set number in the counter and, thereby, by the selected power level. The rectified and duty cycle-modulated half-cycles of the control signal are then filtered to obtain a d.c. bias level which is directly related to the control signal duty cycle. The bias level is employed to control the gain of an r-f amplifier for the cutting signal.

A microprocessor responds to the mode, power and actuation controls for each accessory to provide cutting signals to one accessory at a time in the mode and at the power level selected for that accessory.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components:

FIG. 5 is an electrical schematic diagram of the display board of the electrosurgical generator of the present invention;

FIG. 6 is an electrical schematic diagram of another portion of the display board of the electrosurgical generator of the present invention;

FIG. 8 is an electrical schematic diagram of the high voltage control circuit of the electrosurgical generator of the present invention;

FIG. 15 is a functional block diagram of a portion of the modulator circuit employed in the electrosurgical generator of the present invention;

FIG. 17 is a timing diagram showing various waveforms of signals generated as part of the circuit of FIG. 16;

FIG. 18 is a functional block diagram of another portion of the modulator circuit employed in the electrosurgical generator of the present invention;

FIG. 19 is a functional block diagram of the transistor board circuit employed in the electrosurgical generator of the present invention;

DESCRIPTION OF THE PREFERRED EMBODIMENTS

Figure 1:
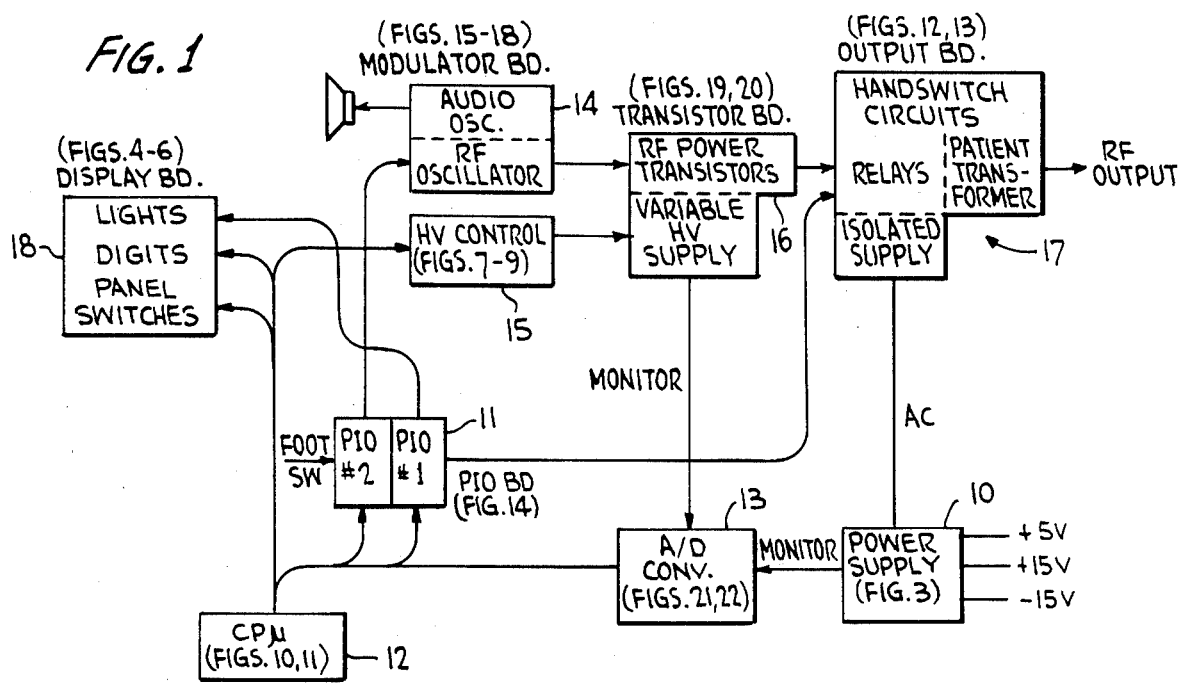
FIG. 1 is a block diagram of the electrosurgical generator of the present invention.

A functional block diagram of an electrosurgical generator constructed in accordance with the present invention is illustrated in FIG. 1 to which reference is now made. The system includes a power supply 10 which is described hereinbelow in greater detail in relation to FIG. 3. The power supply circuit provides three regulated d.c. voltages of +5 volts, +15 volts and −15 volts for internal circuit requirements. In addition, it provides a.c. signals at different levels to effect various control functions in the system, including control over the output r-f power level. The a.c. and d.c. signals are all derived from primary convenience power which may be at 50 Hz or 60 Hz; an adjustment is provided to accomodate the system to either line frequency.

A peripheral input/output (PIO) board 11 provides four eight-bit I/O ports for the system microprocessor. In addition, a four-to-sixteen line decoder controls port selection for the system. The PIO board is described in detail hereinbelow in relation to FIG. 14.

The CPU (central processing unit) circuit 12 contains a Z80-type microprocessor, 1K byte of RAM (random access memory) capacity, 8K bytes of EPROM (erasable programmable read only memory) capacity, a reset circuit, a clock circuit, an address decoder and line driver-buffer circuits. The CPU circuit controls operation of the entire system in response to the positions of the various switches and controls. The CPU circuit is described below in greater detail in relation to FIGS. 10 and 11.

The A/D converter 13 is described below in relation to FIGS. 21 and 22. This circuit contains an eight channel analog-to-digital converter with appropriate support components and buffers to communicate handswitch control information to the CPU circuit 12.

The modulator circuit 14 derives a five hundred KHz base frequency from a 4 MHz clock signal generated in the CPU circuit 12. The five hundred KHz signal constitutes the basic r-f cutting signal which is modulated in timed bursts in accordance with the mode of operation selected at the display board 18. The thusly modulated r-f signal is supplied from the modulator circuit 14 to the transistor board circuit 16 for power amplification before the signal is delivered to the output board for eventual application to the surgical site. The modulator board also contains audio tone generators and amplification components described in detail hereinbelow in relation to FIGS. 15–18.

Figure 9:
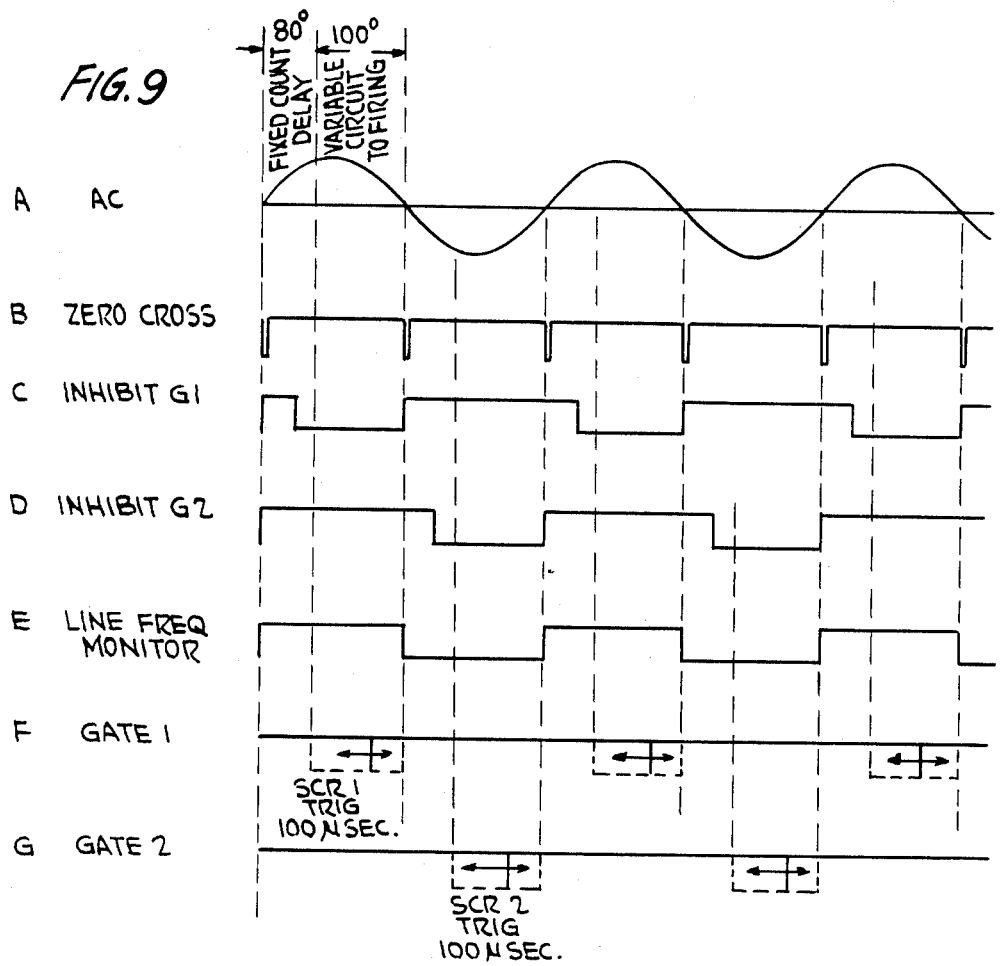
FIG. 9 is a timing diagram showing the waveforms of various signals generated in the circuit of FIG. 8.

The high voltage control circuit 15 is described in detail hereinbelow in relation to FIGS. 7-9. This circuit includes digital phase control circuitry for providing trigger pulses to an SCR full wave bridge rectifier at the transistor board 16. These trigger pulses control the duty cycle for half-cycles of a 50/60 Hz control signal employed ultimately to control the r-f output power level. The time of occurence of the trigger pulses generated at the high voltage control circuit 15 is determined by a pre-set number forced into a counter at the start of each half-cycle of the 50/60 Hz signal. The pre-set number, in turn, is selected at the display board 18 by the operator.

The transistor board 16 contains the r-f power amplifier for the cutting signal, the SCR full wave bridge rectifier described above, monitoring circuits and transistor fail sensing circuitry. The full wave rectified and duty cycle modulated a.c. control signal is filtered to provide a d.c. bias signal having a level proportional to the duty cycle of the a.c. control signal. Since this duty cycle is itself proportional to the selected power level, the d.c. bias level provides an accurate control over the output power for the cutting signal. The transistor board circuit is described in detail in relation to FIGS. 19 and 20.

The output board assembly, described in detail below in relation to FIGS. 12 and 13, contains r-f output amplifiers, high voltage relays, isolated power supplies, and hand-control input circuits. Relay commands from the CPU circuit 12, via the PIO circuit 11, are isolated by appropriate opto-isolators, as are the hand-switch signals applied to the A/D converter 13.

The display board circuitry, described below in relation to FIGS. 4-6, contains the various digital displays, indicator lamps and panel switches employed in the system.

The CPU circuit 12 provides control signals for all system functions. Operator-initiated commands are supplied from hand-operated or foot-operated control accessories via the mode and power switches at the display board 18. All input command switch positions are communicated directly to the CPU circuit.

When the system is idle (i.e., no r-f output signal), the CPU circuit monitors a patient cable, the various hand-switches, the foot-switches and the front panel controls. When a hand or foot switch closure is detected, the CPU circuit 12 commands the relays at the output board 17, via PIO circuit 11, to select an output patient transformer in accordance with the identity of the closed switch. A power control word for the activated operating mode is employed to recall a high voltage control word from the data tables stored in the CPU board circuitry 12. This data word contains SCR phase control information which is written into a data latch at the high voltage control circuit 15. For example, if a TURP (trans-urethral resection procedure) mode is selected, a thirty percent increase in power is calculated and employed for the first three hundred milliseconds of the r-f output signal. This thirty percent increase reduces the "drag" experienced when initiating an underwater cut.

The CPU circuit 12 activates an appropriate tone at modulator board 14, via the PIO circuit 11, to provide an audible indication of the active operating mode. Appropriate wave shape modulation of the r-f signal, in accordance with the selected operating mode, is also effected at the modulator board. The appropriate light at display board 18 is also illuminated at this time.

Only one accessory (e.g., a surgical pencil) and one operating mode may be activated at any one time. The effects of all other switches are locked out until the active accessory is deactivated.

As described below, there are two monopolar accessories and one bipolar accessory usable in connection with the preferred embodiment as disclosed herein. When the monopolar-2 and bipolar modules are simultaneously selected by the module select switch at the display panel, patient cable testing is not initiated unless and until the monopolar accessory is activated. This permits "bipolar-only" operation without connecting a dispersive patient return pad between the patient and the system. All r-f output power signals are mutually isolated and isolated from ground, thereby permitting a combination of bipolar/monopolar operation to be performed without removing the dispersive pad. When the generator is idle, all accessories are disconnected from the r-f amplifier by means of relays under the control of the CPU circuit 12.

Figure 23:
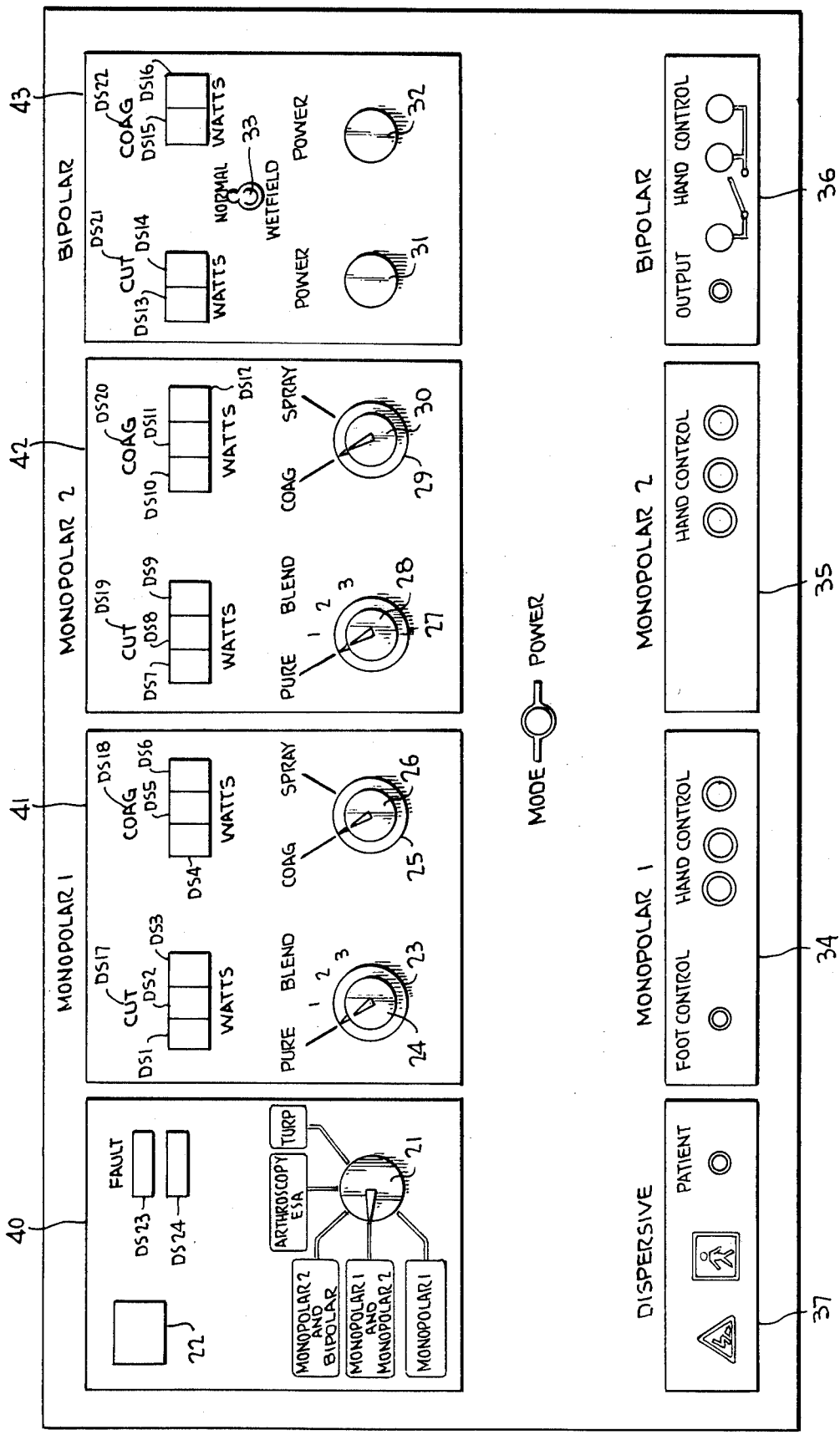
FIG. 23 is a view in plan of the control panel of the electrosurgical generator of the present invention.

The control panel employed in the electrosurgical generator of the present invention is illustrated in FIG. 23 to which specific reference is now made. A module select control switch 21 controls which module or modules are activated and operational at any particular time. There are three such modules, namely: the monopolar-1 module 41; the monopolar-2 module 42; and the bipolar module 43. Each module has its own mode selection and power adjustment controls and is associated with a corresponding accessory connector or connectors. The module select control switch 21 has five distinct positions which are designated as follows: MONOPOLAR-1; MONOPOLAR-1 AND MONOPOLAR-2; MONOPOLAR-2 AND BIPOLAR; ARTHROSCOPY ESA; and TURP. When switch 21 is in the MONOPOLAR-1 position, module 41 is rendered operational and is capable of being activated by either a foot-controlled accessory or a hand-controlled accessory. In the MONOPOLAR-1 AND MONOPOLAR-2 position of switch 21, modules 41 and 42 are rendered operational. Module 41 is capable of actuation in the manner described above; module 42 is capable of activation by means of hand-controlled accessory. In the MONOPOLAR-2 AND BIPOLAR position of switch 21, modules 42 and 43 are operational. As mentioned above, module 42 is capable of activation by means of a hand-controlled accessory. The bipolar module 43 is activated by a foot-control or a bipolar hand-control accessory.

The ARTHROSCOPY ESA position of switch 21 is employed to render the monopolar-1 module 41 operational. Pure cut and coagulation modes are permissable for this switch setting. If any other mode is selected, a flashing occurs at the appropriate indicator signifying that an error has occured; in addition, the unit is rendered inoperative until the error is corrected.

In the TURP position of switch 21, the monopolar-1 module 41 is rendered operational. All cut and coagulation modes are permissable for this switch setting. If a spray mode is selected, the COAG display indicator at the display board flashes to indicate an error condition, and the unit is rendered inoperative until the error is corrected. All of the cut modes include a "rapid start" function during which the power is boosted by thirty percent for approximately three hundred milliseconds at the start of operation up to a maximum output level of three hundred watts.

Located above the module select control switch 21 is a mains power switch 22. This switch is a lighted green rocker type on/off switch having a built-in circuit breaker. This switch is also illustrated as part of the power supply schematic diagram in FIG. 3. To the right of switch 22 on the control panel is a service fault indicator DS24 which is also illustrated as part of the schematic diagram in FIG. 6. This indicator is energized and the unit is rendered inoperative when a failure is detected in the system. Under such circumstances, the cut digit displays DS1, DS2, DS3, DS7, DS8 and DS9 (described below in relation to FIG. 5) display a numeral indicative of the nature of the failure which has occured. The numeral is keyed to a trouble shooting manual supplied for servicing the system.

A cable fault indicator DS23 is located above the service fault indicator DS24 and is energized when a discontinuity has been detected in the patient cable (described below). Energization of indicator DS23 is accompanied by a high-pitched audio tone to alert the operator that a cable fault has been detected. The unit is rendered inoperative until the fault condition is corrected.

A cut-1 indicator DS17 is located in the monopolar-1 module section 41 and is illuminated when any cut mode is activated for the monopolar-1 accessory. Illumination of indicator DS17 is accompanied by an intermediate-pitched audio tone to alert the operator.

A monopolar-1 cut mode select switch 23 selects one of four cutting modes (pure, blend-1, blend-2 and blend-3) for the monopolar-1 accessory. Switch 23 is operative to select the cutting mode only when the module select control switch 21 is in a position which renders the monopolar-1 module 41 operational. In the PURE position of switch 23, a pure cut mode is activated in which hemostasis is provided; the r-f cutting signal is continuous throughout the entire mode. In the BLEND-1 mode, light hemostasis is provided; the sinusoidal r-f signal is on for eighty percent of the time and off for twenty percent of the time. In the BLEND-2 mode, moderate hemostasis is provided; the r-f signal is on for sixty percent of the time. In the BLEND-3 mode, maximum hemostasis is provided and the r-f signal is on for only forty percent of the time.

A cut mode output level control switch 24 for the monopolar-1 module 41 includes a radially small inner control knob disposed concentrically on the cut mode select switch 23. Switch 24 is a three-position switch biased to a center or off position. Switch 24 is also illustrated as part of the circuit of FIG. 5. When rotated to its counterclockwise position, switch 24 causes the power setting for the monopolar-1 cut mode to decrease; when rotated to its clockwise position, switch 24 causes the cut mode power setting for the monopolar-1 module to increase. The power setting increase or decrease is effected by the microprocessor which senses the switch position. When switch 24 is held in its clockwise position, the power setting for the monopolar-1 cut mode increases slowly by up to ten watts; thereafter, if the switch is held in the clockwise position, the power setting increases at a faster rate. A similar operation occurs for decreasing power settings when the switch is turned counterclockwise. When switch 24 is released, it is automatically returned to its center or off position. The power setting may be read on the three cut-1 display digits DS1, DS2 and DS3 located directly above switches 23 and 24 on the control panel. These display digits are illustrated as part of the circuit of FIG. 5 described hereinbelow.

Three coag-1 display digits DS4, DS5 and DS6 are located to the right of the cut-1 digits in the monopolar-1 section of the control panel. The coag-1 digits display the power setting for the coagulate/spray modes of the monopolar-1 accessory. A coag/spray mode selector switch 25 is disposed below the coag-1 digits to permit selection between the coagulate and spray modes. Switch 25, which is also illustrated as part of the circuit of FIG. 5, is a two-position switch and is stable in both positions. In the coag position of switch 25, the accessory for the monopolar-1 module 41 delivers a signal exhibiting moderate sparking for coagulation of a confined area of the surgical site; in this mode, the r-f signal is on for only four percent of the time and off for the remaining ninety-six percent of the time. In the spray mode, maximum sparking is obtained for coagulation of a large area of the surgical site. In the spray mode, the r-f coagulation signal is on for only four percent of the time.

An output power level control switch 26 for the monopolar-1 module 41 is disposed concentrically on switch 25 and is of the same general type as switch 24. In other words, switch 26 is a three-position switch biased to its center or off position and rotatable counter-clockwise to effect a decreasing power setting and clockwise to effect an increasing power setting for the coag/spray modes of the monopolar-1 accessory. A coag indicator lamp DS18 is disposed above the coag-1 display digits and is illuminated (preferably with a blue color) when a coag mode for the monopolar-1 module is activated. Indicator DS18 is illustrated as part of the circuit of FIG. 6.

The monopolar-2 module has control and indicator components which are identical to corresponding control and indicator components for the monopolar-1 module. Thus, the monopolar-2 module 42 includes a monopolar-2 cut output indicator DS19, cut-2 display digits DS7, DS8 and DS9, a monopolar-2 cut mode select switch 27, a monopolar-2 output power level control switch 28, a coag-2 indicator lamp DS20, coag-2 display digits DS10, DS11 and DS12, a monopolar-2 coag/spray mode selector switch 29, and a monopolar-2 coag/spray power level control switch 30.

The controls and indicators at the bipolar module section 43 include a bipolar cut indicator DS21 which illuminates, preferably in a yellow color, when the bipolar cut mode is activated. Display digits DS13 and DS14 for the bipolar cut mode register the power setting for that mode as controlled by the bipolar output power level control switch 31. Switch 31 is the same type of switch as switches 24, 26, 28 and 30, and is used to increase or decrease the cut signal power level for the bipolar module accessory. A bipolar coag indicator lamp DS22 is illuminated when the bipolar coag mode is activated. Immediately below this indicator are the display digits DS15 and DS16 for the bipolar coag power setting. A bipolar coag output power level control switch 32, of the same general type as switch 31, controls the output power level in the bipolar coag mode. A bipolar output impedance selector switch 33 includes a normal position in which the output impedance is set at three hundred ohms and a wetfield position in which the output impedance is set at fifty ohms. The normal position is used when coagulation of higher impedance tissue is desired. The wetfield position is used when coagulation of low impedance tissue is required.

All of the control switches described above have their settings sensed by the microprocessor so that the desired modes are established and power settings effected by software control.

A monopolar-1 accessory receptacle 34 is provided for connection to a three-prong hand-control or single-prong foot-control monopolar surgical pencil, or other similar accessory. The monopolar-2 accessory receptacle 35 is provided for connection to a three-prong hand-control monopolar accessory. The bipolar accessory receptacle 36 is provided for connection to a three-prong hand-control or two-prong foot-control bipolar accessory. A dispersive patient receptacle 37 is provided for connection to a patient return cable which connects the dispersive patient pad back to the unit. This cable is utilized when the module select control switch 21 is set to the MONOPOLAR-2 AND BIPOLAR position and a monopolar accessory is to be used.

The existance of any cut mode (monopolar or bipolar) is accompanied by an intermediate-pitched audio tone; the existance of any coagulation/spray mode (monopolar or bipolar) is accompanied by a low-pitched audio tone. A high-pitched audio tone sounds when a patient cable fault has been detected. Each of these three tones has a distinct sound so that the nature of the identified condition will be evident to the operator. For example, the high-pitched tone may typically be at 2 KHz; the intermediate-pitched tone is typically at 1 KHz and the low-pitched tone is typically at 500 Hz. These tones are generated in the circuit illustrated in FIG. 16.

Figure 2:
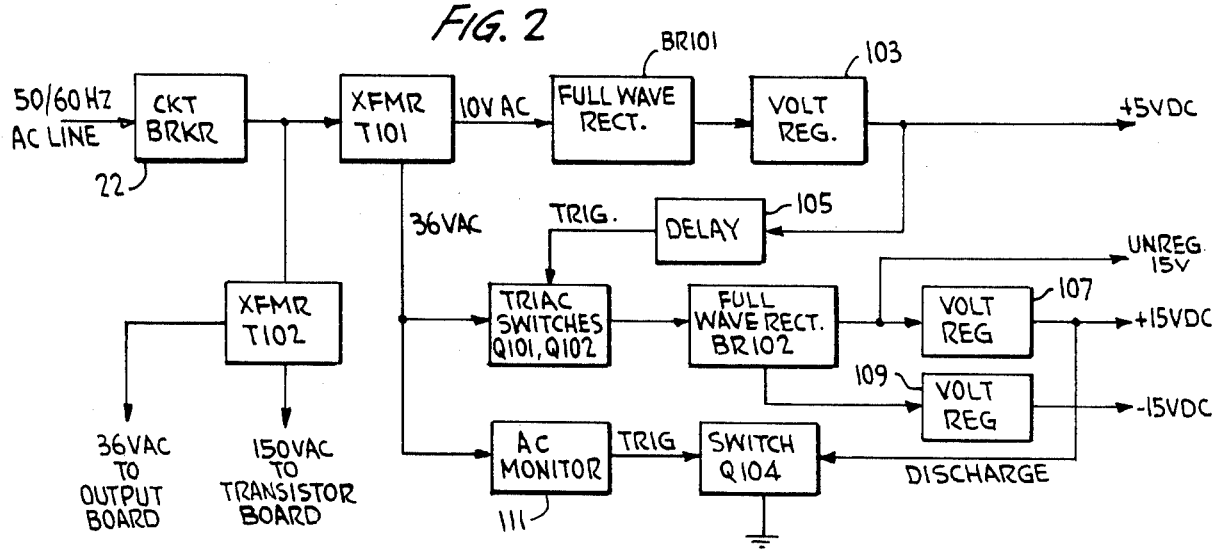
FIG. 2 is a block diagram of the power supply portion of the system of the present invention.

A block diagram for the power supply assembly of the electrosurgical generator is illustrated in FIG. 2 to which specific reference is now made. The primary power a.c. line at 50/60 Hz is applied through a circuit breaker 22 to each of two transformers T101 and T102. Transformer T101 provides a ten volt a.c. output signal which is rectified in a full wave rectifier bridge BR101. The output of bridge BR101 is applied to a voltage regulator 103 to supply the +5 volts d.c. voltage for the system. The +5 volt d.c. signal is applied through a delay circuit to trigger each of triac switches Q101 and Q102. These switches pass a thirty-six volt a.c. output signal also provided by transformer T101 to a full wave rectifier bridge BR102. The output of full wave rectifier bridge BR102 is an unregulated 15 volt d.c. signal. This unregulated 15 volts d.c. signal is applied through a voltage regulator 107 to provide a +15 volts d.c. line for the system. This voltage is applied to a switch Q104. The thirty-six volts a.c. output voltage from transformer T101 is also applied to an a.c. monitor circuit 111 which also provides a trigger signal to switch Q104.

Transformer T102 provides a thirty-six volt a.c. output voltage to the system output board, and a 150 volt a.c. output voltage to the system transistor board.

Figures 3, 4:
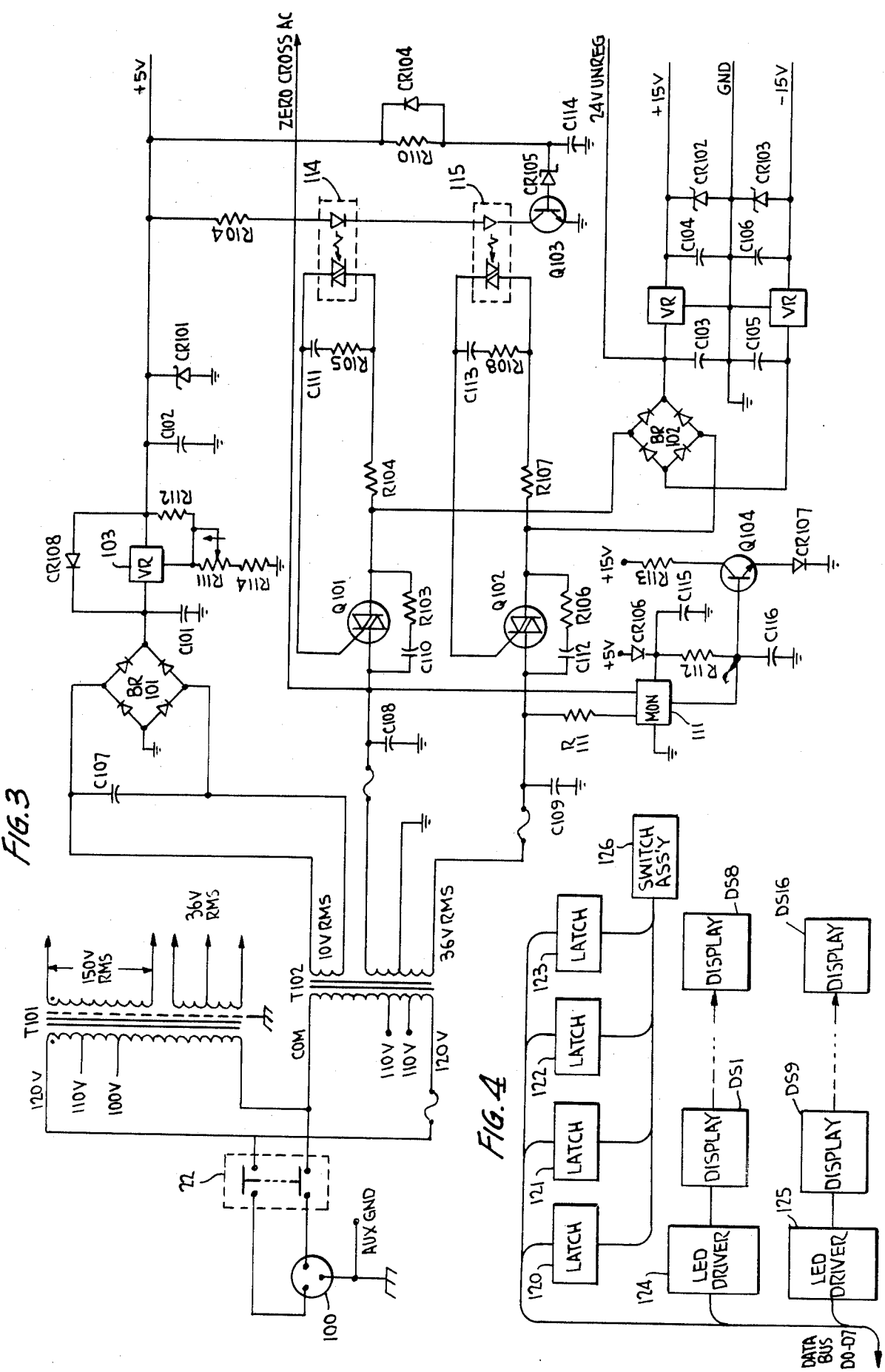
FIG. 3 is a schematic diagram of the power supply portion of the electrosurgical generator of the present invention.
FIG. 4 is a functional block diagram of the display board of the electrosurgical generator of the present invention.

The detailed schematic diagram for the power supply circuit is illustrated in FIG. 3 to which specific reference is now made. A primary power receptacle receives the 50/60 Hz signal and connects both lines through respective contacts of circuit breaker 22. The primary a.c. power is supplied to the primary windings of transformers T101 and T102. One secondary winding of transformer T101 provides the 150 volts rms output voltage for the transistor board circuit. The other secondary winding for transformer T101 provides the thirty-six volts rms voltage for the output board circuit.

One secondary winding of transformer T102 provides the ten volts rms signal which is applied across capacitor C107 to a full wave diode bridge rectifier BR101. The rectified output voltage from this bridge is applied across capacitor C101 to a voltage regulator 103 having a diode CR108 connected between its output and input terminals. The regulated output voltage from regulator 103 is coupled through resistor 112, potentiometer R111 and resistor R114 to circuit ground. In addition, the output voltage from regulator 103 is connected across capacitor C102 to ground and across zener diode CR101 to ground. The resulting regulated +5 volts d.c. is utilized throughout the system as a +5 volts d.c. source. This voltage is also coupled to ground through a series circuit including resistor R104, a light emitting diode (LED) in an opto-isolator 114, a second LED in opto-isolator 115, and the collector-emitter path through an NPN transistor Q103. A further path to ground for the regulated +5 volts d.c. is provided by resistor R110 connected in parallel with reverse polarity diode CR104, the combination connected in series with capacitor C114. A zener diode CR105 has its cathode connected to the junction between capacitor C114 and the resistor R110. The anode of zener diode CR105 is connected to the base of transistor Q103.

A second secondary winding of transformer T102 provides two phases of thirty-six volts rms voltage referenced to a center tap of the secondary winding which is connected to ground. One phase of thirty-six volts rms voltage is: (1) applied across capacitor C108 to circuit ground; (2) supplied to the high voltage circuit (FIGS. 7-9) as the power line frequency reference signal for zero crossing detection; (3) connected to the cathode of a silicon controlled rectifier (SCR) Q101; and (4) connected to one input terminal of the a.c. monitor 111. A capacitor C110 and a resistor R103 are connected in series across the anode and cathode of SCR Q101. The anode of SCR Q101 is also connected to one input terminal of a full wave diode bridge rectifier BR102. The gate electrode of SCR Q101 is connected to one side of a parallel circuit which includes the photo-sensitive element in opto-isolator 114 as one parallel path connected across the series combination of a capacitor C111 and resistor R105. This parallel circuit is connected in series with a resistor R104 which has its other end connected to the anode of SCR Q101. The other phase of the thirty-six volts rms line is similarly connected, except for the zero crossing referenced, as follows: across capacitor C109 to circuit ground; to the cathode of SCR Q102; and to the other input terminal of the a.c. monitor circuit 111 via resistor R111. A series circuit including capacitor C112 and resistor R106 is connected across the anode and cathode of SCR Q102. The anode of SCR Q102 is connected to the other side of the full wave diode bridge rectifier BR102. The gate electrode of SCR Q102 is connected to one side of a parallel circuit including the photo-sensitive element in opto-isolator 115 as one branch, and the series circuit including a capacitor C113 and resistor R108 in the other branch. This parallel circuit has its other end connected to resistor R107 which is returned to the anode of SCR 102.

The a.c. monitor circuit 111 is biased by the +5 volts supply through a diode CR106, the cathode of which is capacitively returned to circuit ground via capacitor C115. The output terminal of the a.c. monitor circuit 111 is applied across capacitor C116 to the base electrode of an NPN transistor Q104, the emitter of which is coupled to ground through forward biased diode CR107. The high sides of capacitors C115 and C116 are resistively coupled via resistor R112. The cathode of transistor Q104 is resistively coupled to the +15 volts d.c. line through a resistor R113.

Figure 21:
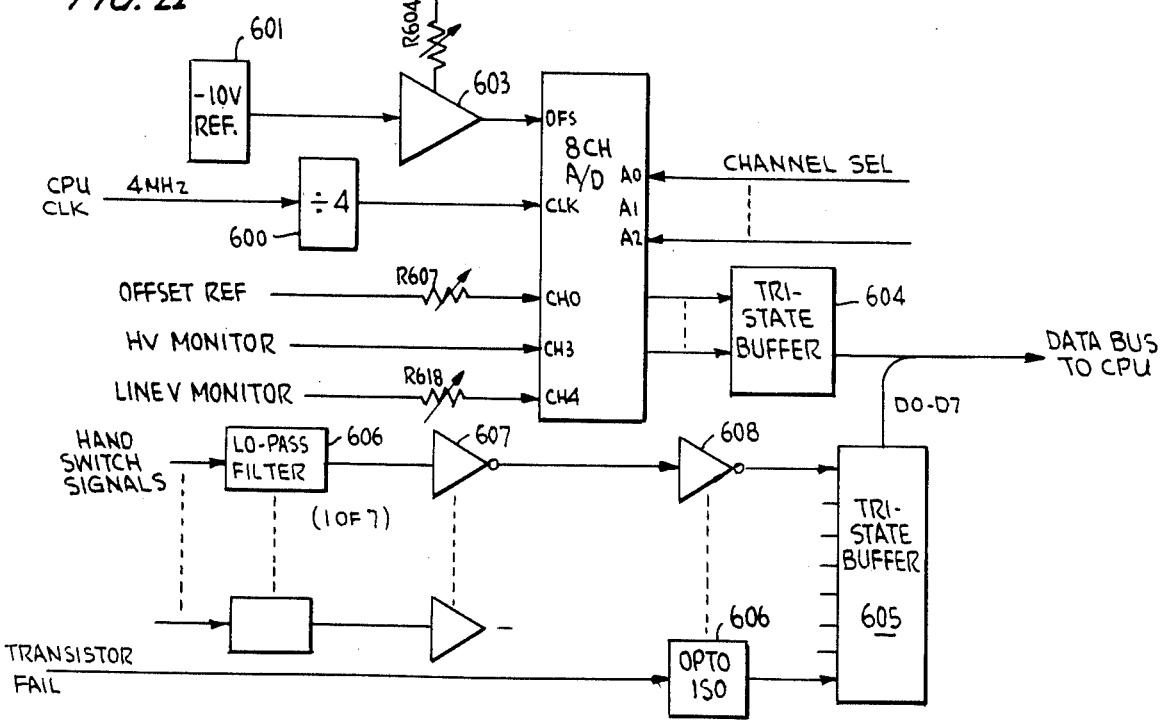
FIG. 21 is a functional block diagram of the analog-to-digital converter circuit employed in the electrosurgical generator of the present invention.
Figure 22:
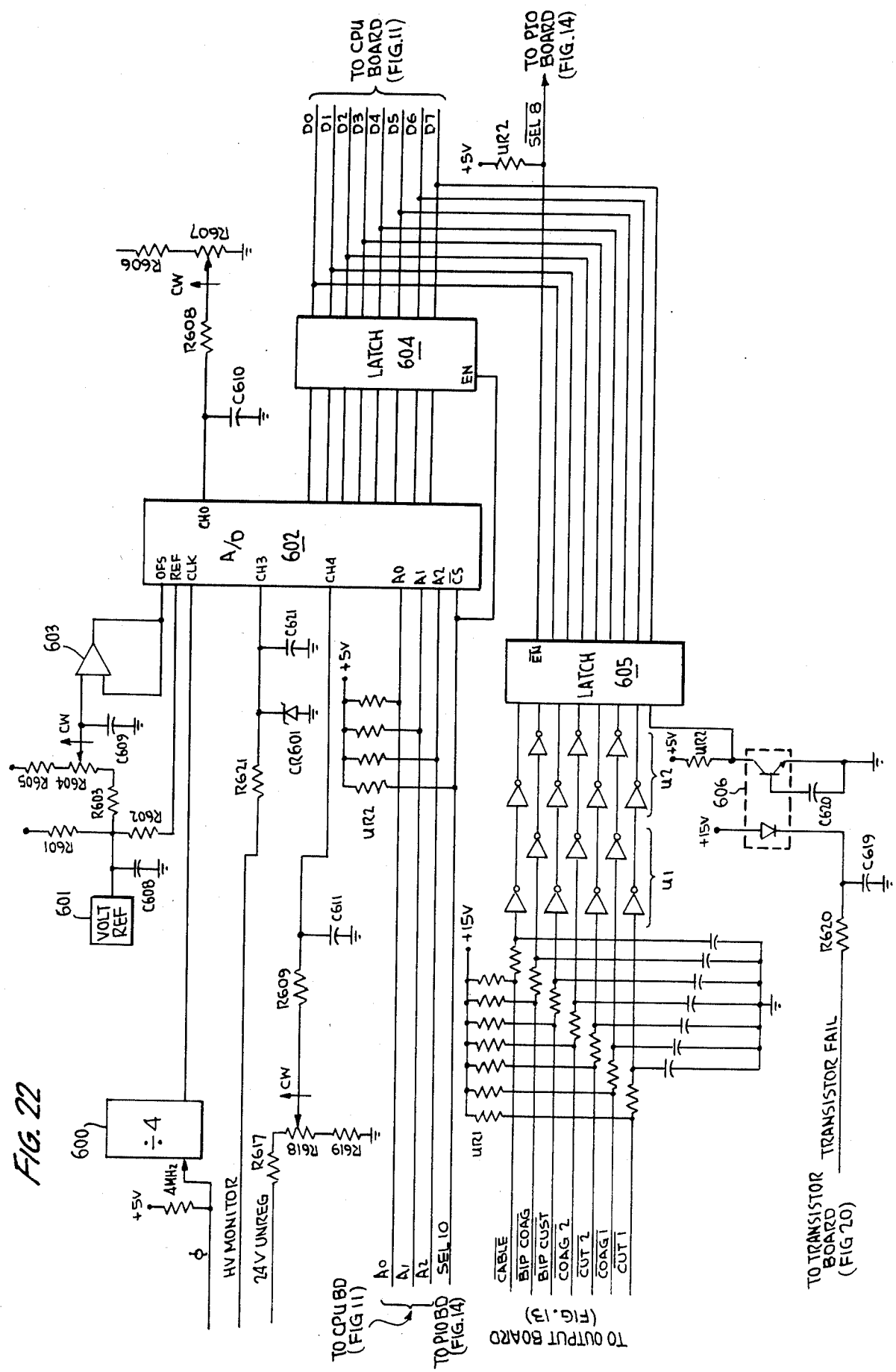
FIG. 22 is an electrical schematic diagram of the analog-to-digital converter circuit employed in the electrosurgical generator of the present invention.

The positive output terminal of bridge BR102 provides a twenty-four volts d.c. unregulated line utilized at the transistor board circuit (FIGS. 19, 20) and the A/D converter circuit (FIGS. 21, 22). The positive output voltage from bridge BR102 is also connected to the input terminal of voltage regulator 107 and to one side of a capacitor C103, the other side of which is coupled to circuit ground. The negative output terminal of bridge BR102 is connected to an input terminal of voltage regulator 109 and to one side of a capacitor C105, the other side of which is coupled to circuit ground. The output terminal of voltage regulator 107 is connected to one side of a capacitor C104 and to the cathode of a zener diode CR102, the anode of which is connected to circuit ground as is the other side of capacitor C104. The output line from voltage regulator 107 comprises the regulated +15 volt supply line utilized by various circuits in the system.

The output signal from voltage regulator 109 is connected across capacitor C106 to ground and across another zener diode CR103, connected anode-to-cathode, to ground. This regulated output voltage comprises the −15 volt supply utilized in the system.

In operation, it may be seen that the power supply circuit, illustrated in FIGS. 2 and 3, furnishes three regulated d.c. voltages of +5 volts, +15 volts and −15 volts for system requirements. The + and −15 volt supplies are delayed at turn on by the +5 volt supply to permit the microprocessor circuit to reset and initialize its input/output ports before other circuits are energized. This delay is established by resistor R110 and capacitor C114. Capacitor C114 is charged by the +5 volts d.c. supply until zener diode CR105 and transistor Q103 are rendered conductive which occurs at approximately 4.3 volts. When transistor Q103 conducts, the photo-sensitive elements in opto-isolators 114 and 115 are rendered conductive to trigger SCR Q101 and SCR Q102 into conduction, thereby providing primary power for the +15 volt and −15 volt supplies.

The a.c. monitor 111 serves as a line monitor for the primary power. As long as a.c. voltage is present across input lines 117 and 118 for the monitor, the output terminal of the monitor, connected across capacitor C116, is held at a low logic level to bias transistor Q104 into its non-conductive state. If a.c. power is removed across lines 117 and 118, the output signal from monitor 111 becomes high and allows capacitor C115 to discharge through resistor R112. The result renders transistor Q104 conductive and discharges the +15 volt d.c. supply through resistor R113, transistor Q104 and diode CR107. Discharging the +15 volt d.c. supply insures that it reaches 0 volts before the +5 volt d.c. supply decays to the point where the microprocessor circuitry looses control.

The functional block diagram of the display board circuit 18 of FIG. 1 is illustrated in FIG. 4 to which specific reference is now made. The display board contains two eight-digit LED drivers 124 and 125, four tri-state latch units 120, 121, 122 and 123, a switch assembly 126, the individual digital display units DS1–DS16, and indicator lamps and drivers (not illustrated in FIG. 4). Switch assembly 126 corresponds to the switches described above in relation to the control panel of FIG. 23. The states of the switches are stored in the latches 120, 121, 122 and 123 from which the microprocessor reads the switch states. The position of each switch is represented as a single binary bit. When one of the latch units 120, 121, 122 and 123 is addressed, a group of eight switch positions, in the form of respective bits, is placed on the data bus (lines D0–D7).

Referring to FIG. 5 of the accompanying drawings, the detailed schematic diagram shows each of the switches 21, 23, 24, 25, 26, 27, 28, 29, 30, 31, 32 and 33 individually. As noted above, these switches correspond to the switch assembly illustrated in FIG. 4. The arm of each switch is connected to circuit ground. The contact for each switch position is connected to a respective latch input terminal in the latch units 120, 121, 122 and 123. These switch contacts are also connected through respective individual resistors (nominally 2.2 Kohms) to the +5 volts d.c. supply. The input terminals of the latches 120, 121, 122 and 123 are normally maintained at a high logic level. When a switch is actuated to any contact position, the corresponding latch input terminal is tied to circuit ground to provide a low logic level at that input terminal. The status of each latch is periodically sampled by the microprocessor in conjunction with the select lines connected to the individual latch circuits. In other words, the $\overline{SEL2}$, $\overline{SEL9}$, $\overline{SEL6}$ and $\overline{SEL7}$ signals are selectively driven low to address respective latch circuits 120, 121, 122 and 123. This periodic addressing of the latch circuit states permits the states of the control switches to be read by the microprocessor. The latch circuits 120, 121, 122 and 123 are preferably Model 74LS245 Tri-State Octal Buffers.

Each LED driver circuit 124 and 125 is preferably a Model ICM7218C and contains an eight-by-four bit RAM memory. Data to be displayed is written as a four-bit word. The low four bits D0–D3 contain the number to be written; the high four bits D4–D7 contain the address for the internal RAM location. Each of the four-bit words are multiplexed to the seven LED segments in each of the display digits at a 2 KHz rate by a clock internal to the driver circuit.

Referring to FIG. 6, the various status indicator lamps at the display panel include lamps DS17–DS24, inclusive. One side of each of these status indicator lamps is connected to the +15 volts d.c. supply through a resistor. The other side of the lamp is connected to the output terminal of a respective lamp driver amplifier which is fed by the corresponding status signal provided by the PIO circuit of FIG. 14. The individual drivers effectively convert the 5 volt status signals to a 15 volt level required by the lamps.

Figure 7:
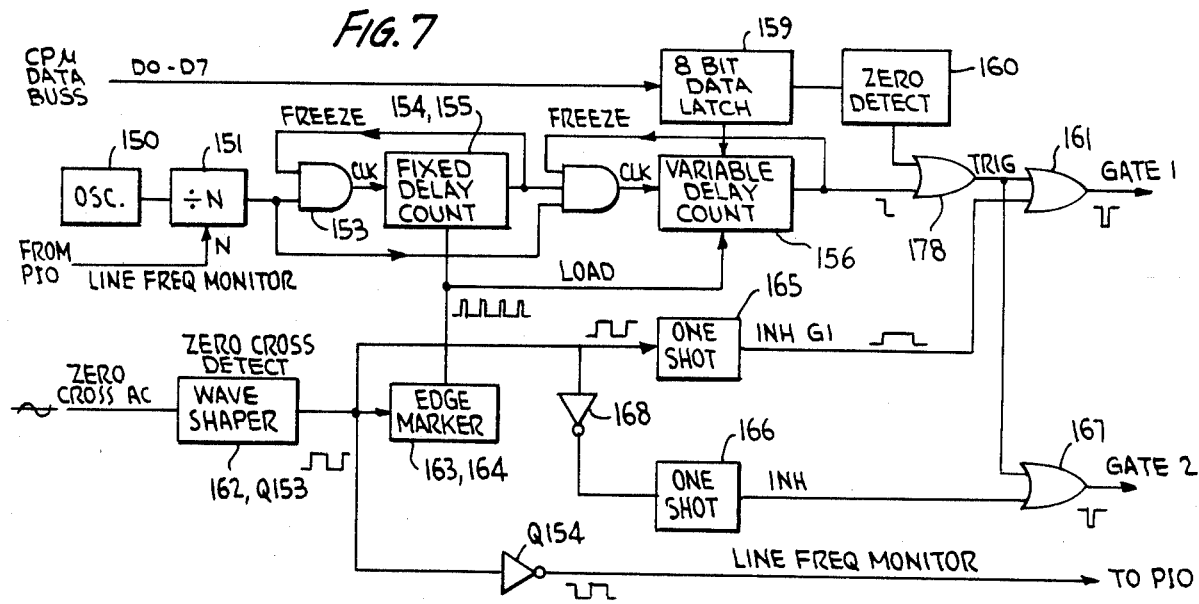
FIG. 7 is a functional block diagram of the high voltage control circuit of the electrosurgical generator of the present invention.

Reference is now made to the high voltage control board circuitry illustrated in block diagram form in FIG. 7 and in detailed schematic form in FIG. 8. The primary function of the high voltage control circuitry is to control the phase for triggering the SCR bridge rectifier at the transistor board (FIGS. 19, 20) so that the variable output level from this bridge can control the r-f power level. The circuit includes an oscillator 150 which, in the preferred embodiment, provides output pulses at a repetition frequency of 277.65 KHz. These pulses are applied to a divide-by-N counter 151 which is preferably a Model 4526 Programmable Counter. Counter 151 is pre-set by the line frequency select signal received from the PIO circuit (FIG. 14) which indicates whether or not the primary power for the system is derived from 50 Hz or 60 Hz a.c. power lines. For 60 Hz power, a divide-by-five factor is employed in counter 151; for 50 Hz power, a divide-by-six factor is employed. Thus, the output pulse train from counter 151 has a frequency of 55.5 KHz for sixty cycle power and 46.3 KHz for fifty cycle power. This adjustment for primary power frequency maintains the firing angle constant for the SCR bridge at the transistor board (FIG. 20) in the manner described below.

As illustrated in FIG. 7, the output pulse train from counter 151 is gated by means of gate 153 to supply clock pulses to a fixed delay counter 154, 155. In addition, the output pulse train is gated by counter 156 to provide clock pulses to a variable delay counter 157, 158. In the detailed schematic diagram of FIG. 8, gate 153 is seen to be a two-input NAND gate which receives the clock pulse train from counter 151 at one of its input terminals via an inverter. The inverted clock pulses are also applied to one input terminal of gate 156 which, as seen in FIG. 8, is a four-input NAND gate. The output signal from NAND gate 153 is inverted and applied to the clock input terminals of each of counters 154 and 155 which correspond to the fixed delay counter illustrated in FIG. 7. These counters are preferably Model 4029 type counters and are pre-set with a fixed count each time a pulse is received at its PE (pre-set enable) terminal. Counters 154 and 155 are cascaded by connecting the CO output terminal of counter 154 to the CI terminal of counter 155. When a predetermined count is achieved at counters 154 and 155, an eight-input NAND gate 170 is enabled and delivers its output signal as the second input signal to NAND gate 153 to prevent further counting of clock pulses at counters 154 and 155. The output signal from NAND gate 170 is also inverted and applied as a second input signal for NAND gate 156.

When NAND gate 156 is enabled, count pulses from counter 151 are applied to the CLK terminals of counters 157 and 158 which are connected in cascade and which are of the same general type as counters 154 and 155. Counters 157 and 158 are pre-set with a variable count via the eight-bit latch circuit 159 which receives signals from the microprocessor on the data bus (D0-D7). Latch circuit 159 is preferably a Model 74LS373 Tri-State Octal Latch which provides the pre-set bits to counters 157 and 158 via respective drivers. When the output count from counters 157 and 158 achieves a predetermined count value, an eight-input NAND gate 169 provides a low output signal to a third input terminal of NAND gate 156, corresponding to the freeze signal shown at gate 156 in FIG. 7. The low level output signal from NAND gate 169 is also applied through capacitor C158 to one input terminal of a two-input NOR gate 178 which corresponds to the trigger gate 178 in FIG. 7. The second input signal for NOR gate 178 is derived from an eight-input NOR gate 160 which receives the individual pre-set bits applied to counters 157 and 158 as its input signals. The output signal from NOR gate 178 is applied to one input terminal of each of two-input NOR gates 161 and 167 via an inverter.

The ZERO CROSS A.C. line from the power supply circuit (FIG. 3) is applied through resistor R157 to the non-inverting input terminal of an operational amplifier comparator 162. That terminal is connected to resistor R158 which is returned to circuit ground as the inverting input terminal of amplifier 162. The output terminal of amplifier 162 is positively biased by the +15 volt d.c. supply through resistor R159 and is coupled to the base of transistor Q153 through a resistor R160. Transistor Q153 is an NPN transistor having an emitter coupled to circuit ground and a collector coupled through resistor R161 to the +15 volt d.c. supply. In addition, the collector of transistor Q153 is connected to one side and the wiper arm of a potentiometer R162, the other side of which is connected to a resistor R163. The other side of resistor R163 is connected across capacitor C157 to circuit ground. Resistor R163 is also connected to one input terminal of a two-input exclusive OR gate 164. The second input terminal of exclusive OR gate 164 is connected to the +15 volt supply, while the output signal from exclusive OR gate 164 is connected as one input signal to a two-input exclusive OR gate 163. The other input terminal of gate 163 is connected to the junction between resistors R161 and R162. The circuitry associated with gates 163 and 164 serve as an edge marker for zero crossing detection of the primary power voltage. The output signal from exclusive OR gate 163 is applied, via an inverter, to the MR terminal of counter 151 to reset that counter, and to the PE terminals of counters 154, 155, 157 and 158 to initialize and pre-set those counters with the pre-set bits applied thereto. The output signal from exclusive OR gate 163 is also connected as the final input to the four-input NAND gate 156.

Figure 20:
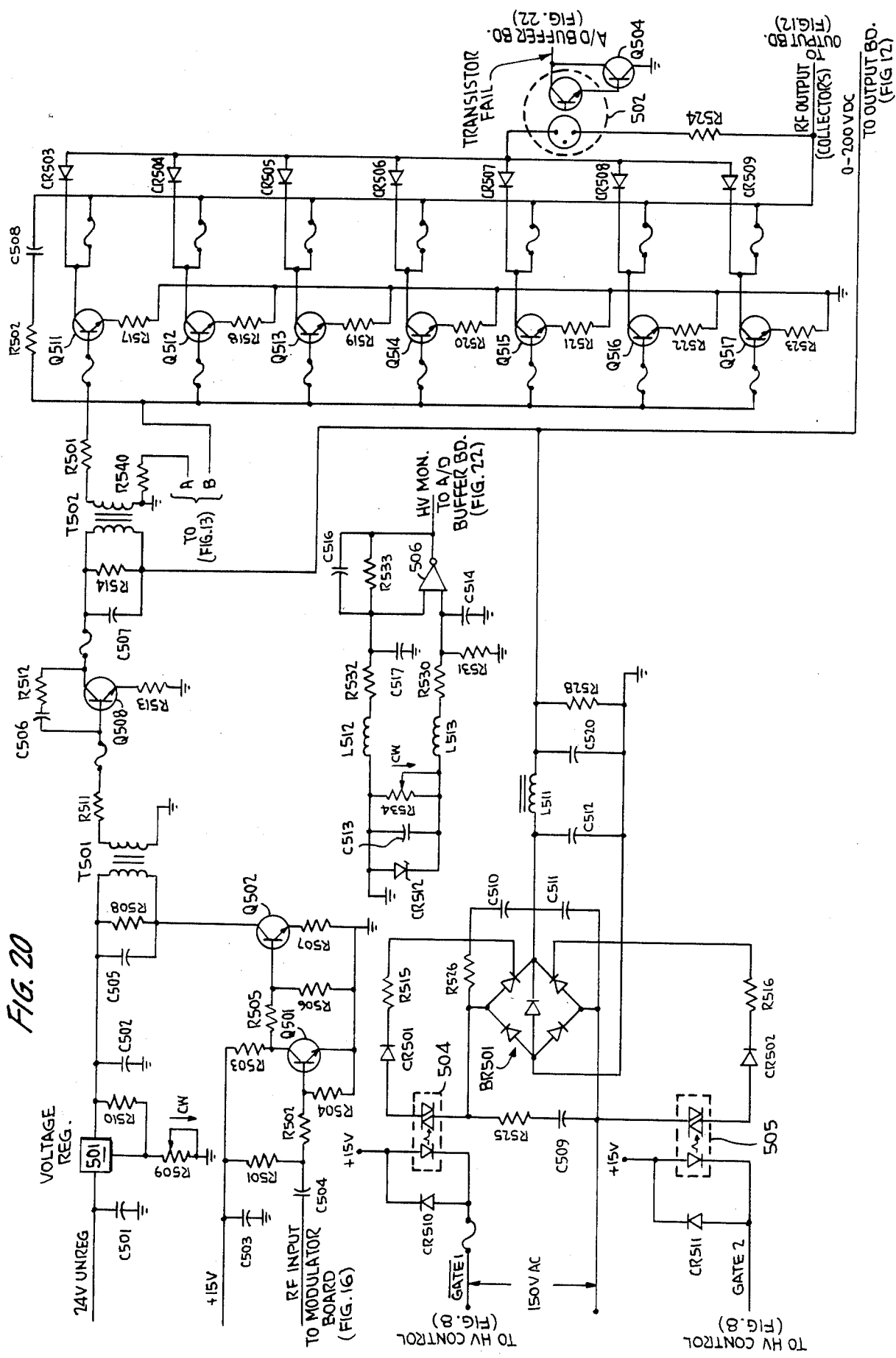
FIG. 20 is an electrical schematic diagram of the transistor board circuit employed in the electrosurgical generator of the present invention.

The collector of transistor Q153 is applied as an input signal to a one-shot multivibrator 165 and to one input terminal of a two-input exclusive OR gate 168. Exclusive OR gate 168 serves as an inverter for driving a further one-shot multivibrator 166. The output signals from one-shot multivibrators 165 and 166 are applied as the second input signals to NOR gates 161 and 167, respectively. The output signal from NOR gate 161 is applied through resistor R160 to the base of transistor Q155 which is an NPN transistor having its emitter coupled to circuit ground and its collector coupled through resistor R162 to the transistor board circuitry (FIG. 20). A capacitor C163 is connected between the collector and emitter electrodes of resistor Q155. The output signal from NOR gate 167 is coupled through resistor R161 to the base electrode of a further NPN transistor Q156 which has its emitter connected to circuit ground and its collector connected through R173 to the transistor board circuit of FIG. 20. A capacitor C164 is connected between the collector and emitter of transistor Q156.

Figure 14:
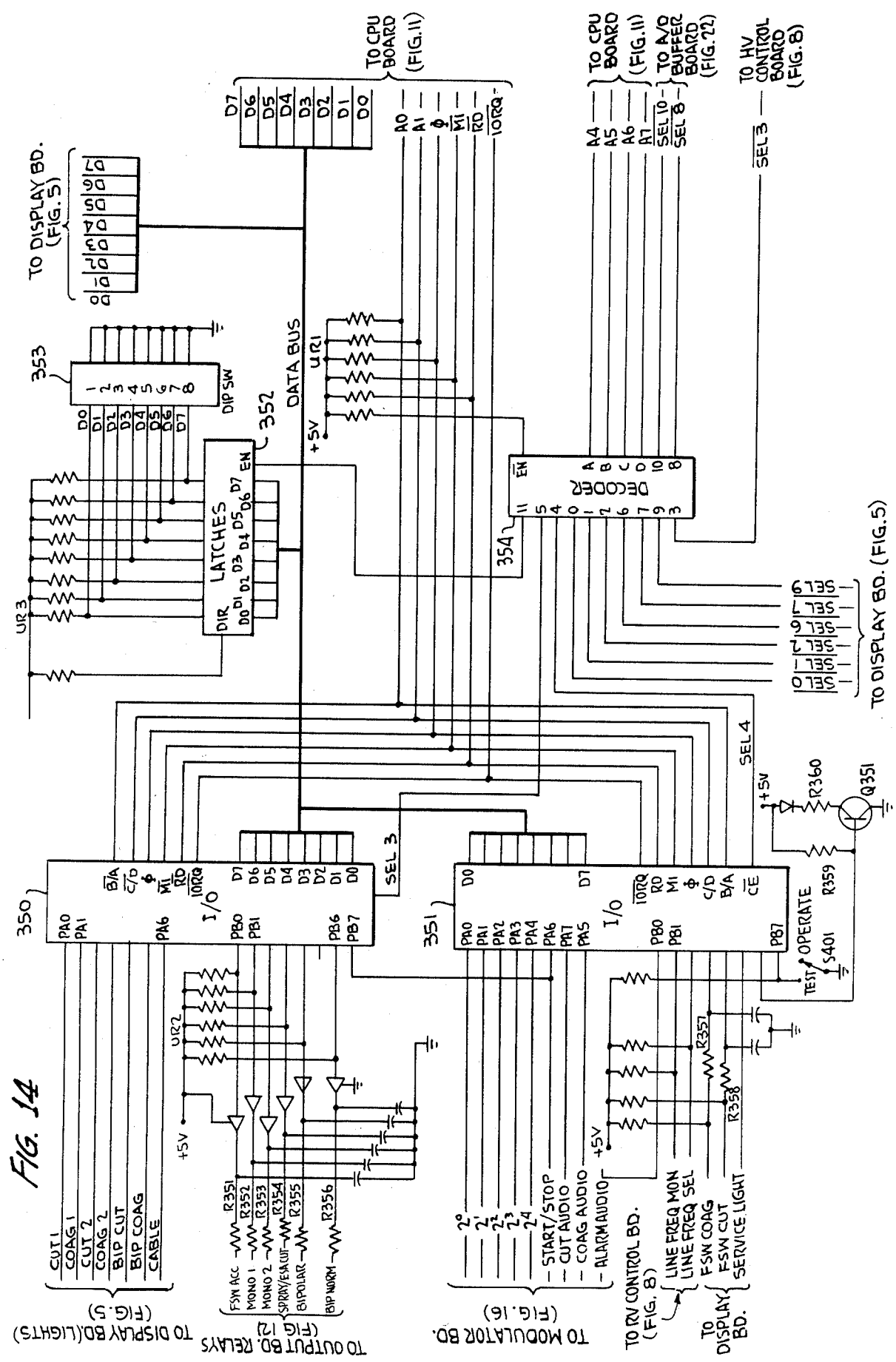
FIG. 14 is an electrical schematic diagram of the peripheral input-output (PIO) board circuit employed in the electrical generator of the present invention.

The collector of transistor Q153 is also connected through resistor R164 to the base electrode of transistor Q154, another NPN transistor having a grounded emitter and having its collector connected to the PIO circuit of FIG. 14.

The operation of the circuit illustrated in FIGS. 7 and 8 will now be described in conjunction with the timing diagram of FIG. 9 wherein the various signals are identified by letters A-G shown at appropriate circuit points in FIG. 8. When the electrosurgical generator is idle and provides no r-f output signal, the microprocessor provides a zero count on bits D0-D7 to latch 159. NOR gate 160 blocks the generation of trigger pulses at gates 161 and 167, via gate 178, when a logic zero is present in latch 159. This blocking or inhibition of trigger pulses is effected by providing a binary one signal from gate 160 at the corresponding input terminal of gate 178 to prevent passage of trigger pulses upon termination of the count at counters 157 and 158.

Upon activation of an accessory switch at the control panel, the microprocessor reads the mode and power setting for that accessory in order to reference a phase control word in the memories associated with the microprocessor. This word is then written into the eight-bit latch 159 via the data bus bits D0–D7. At the next zero crossing of the ZERO CROSS AC signal, designated signal A in FIG. 9, the eight bits present in latch 159 are loaded into counters 157 and 158. This zero crossing is determined by means of the circuitry associated with amplifier 162 and transistor Q153 which transforms the sinusoidal a.c. signal into a square wave having the same frequency as the a.c. line. This square wave signal is illustrated as signal E in FIG. 9. The EXCLUSIVE OR gates 163 and 164 operate on the square wave to provide negative-going triggers (signal B in FIG. 9) at the zero crossing between each half-cycle of the a.c. line signal. These negative-going triggers are applied through an inverter to each of the PE (pre-set enable) terminals of counters 154, 155, 157 and 158 to load the appropriate pre-set count into these counters. In this manner, the bits present in latch 159 are pre-set into counters 157 and 158. In addition, the hard-wired count is pre-set, at the zero crossing time, into counters 154 and 155. The purpose of the hard-wired count in counters 154 and 155 is to delay the clock pulses from reaching the programmed counters 157 and 158 for the first eighty degrees of each a.c. line half-cycle. In other words, the clock pulses from counter 151 are blocked from application to the CLK terminals of counters 157 and 158 by NAND gate 156 until the output count in counters 154 and 155 actuate NAND gate 170. By pre-setting counters 154 and 155 with an appropriate count at the start of each half-cycle, the time at which NAND gate 170 is actuated corresponds to eighty degrees of the a.c. line frequency. Actuation of NAND gate 170 also disables NAND gate 153 so that further clock pulses cannot be applied to counters 154 and 155 to further increase the count in those counters until the start of the next half-cycle. Once the counters 157 and 158 begin counting clock pulses (i.e., after the first eighty degrees of the a.c. line frequency), the bits from latch 159, which have been pre-set into counters 157 and 158, determine the time at which the count in counters 157 and 158 actuate NAND gate 169 to provide a trigger pulse through capacitor 158 to NOR gate 168. Specifically, NAND gate 169 provides a negative-going output signal when the count in counters 157 and 158 reaches the preselected value. The falling edge is differentiated by means of capacitor C158 and resistor R165 to form a firing pulse of approximately sixty-eight microsecond duration. In addition, actuation of NAND gate 169 inhibits further count of clock pulses at counters 157 and 158 by disabling NAND gate 156. Thus, after the firing pulse has been provided by the actuated gate 169, all of the counters are maintained in a non-counting mode by their own count status. Upon the next zero crossing detection (i.e., at the start of the next half-cycle of the a.c. line signal), the trigger pulse B is applied to each of the PE terminals of counters 154, 155, 157 and 158 to pre-set these counters and thereby change the count status. This change in count status permits the clock pulses from counter 151 to be counted, first at counters 154 and 155, and then, after a delay of eighty degrees, at counters 157 and 158.

The one-shot circuits 165 and 166 are triggered in response to opposite half-cycles of the square wave signal E. The one-shot multivibrator 165 is triggered by the rising edge of the square wave signal E to provide a pulse C of approximately eleven milliseconds duration. The one-shot multivibrator 166 receives the square wave through EXCLUSIVE-OR gate 168 connected as an inverter so that this one-shot multivibrator is triggered by the falling edges of the square wave E. The output signal from one-shot multivibrator is also an eleven milliseconds pulse, designated as signal D, and displaced 180° (relative to the a.c. line frequency) from the pulse signal C. The duration of eleven milliseconds for the pulses in signals C and D is slightly longer than a half-cycle of the a.c. line frequency. Consequently, the pulses C are effective at gate 161 to inhibit that gate from passing the firing pulses from gate 168 during alternate half-cycles of the square wave E. The other alternate half-cycles are blocked by the signal pulses D at gate 167. Thus, the firing pulses F and G provided from transistor Q155 and Q156, respectively, appear in alternate half-cycles of the square wave E. As illustrated in FIG. 9, these pulses F and G can occur anywhere within the last one hundred degrees of their respective half-cycles of the a.c. line frequency, depending upon the count which is pre-set into counters 157 and 158. As described below, pulses F and G are employed to trigger respective SCR's in a full wave rectifier bridge, to control the duty cycle of that bridge when acting upon a signal having the same frequency as the square wave E. The resulting duty cycle modulation controls the energy applied to a filter to in turn control the d.c. level of a bias signal used for the amplifiers for the r-f cutting signal. The r-f drive level is thereby fixed by means of this digital phase control technique which eliminates drift that is inherent in analog-to-digital converters. The accuracy of the delivered r-f power in the cutting signal is thereby improved significantly. The elimination of the first eighty degrees of each half-cycle (by means of the fixed pre-set count in counters 154 and 155) has the advantage of providing increased resolution in the duty cycle and power level control from the latched eight-bit word. Specifically, control is effected over only one hundred degrees, rather than one hundred eighty degrees of the half-cycle. The first eighty degrees includes no appreciable increase in power over the remaining one hundred degrees. The precision control, however, is extremely advantageous since power settings are critical, particularly at low power levels, for delicate surgery. In fact, the low power levels are inherently the most difficult power levels to control in electrosurgery.

Figure 10:
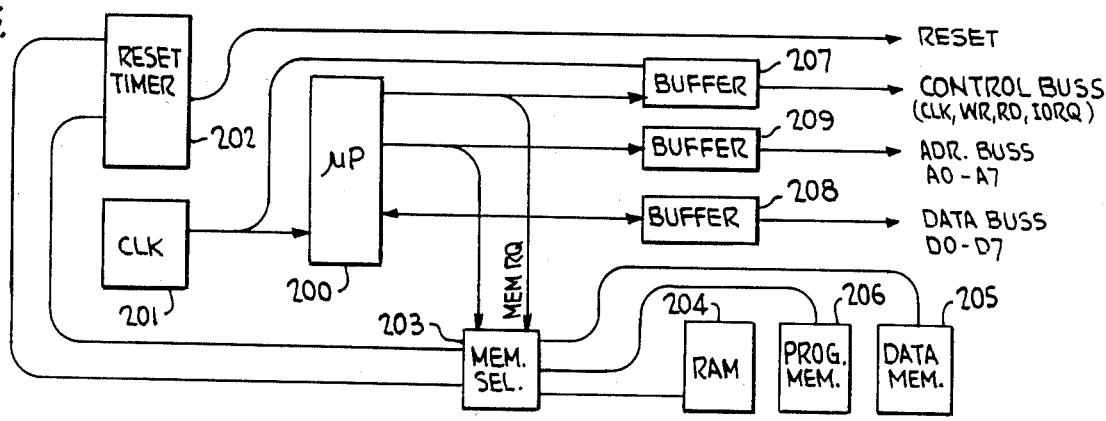
FIG. 10 is a functional block diagram of the central processing unit employed in the electrosurgical generator of the present invention.
Figure 11:
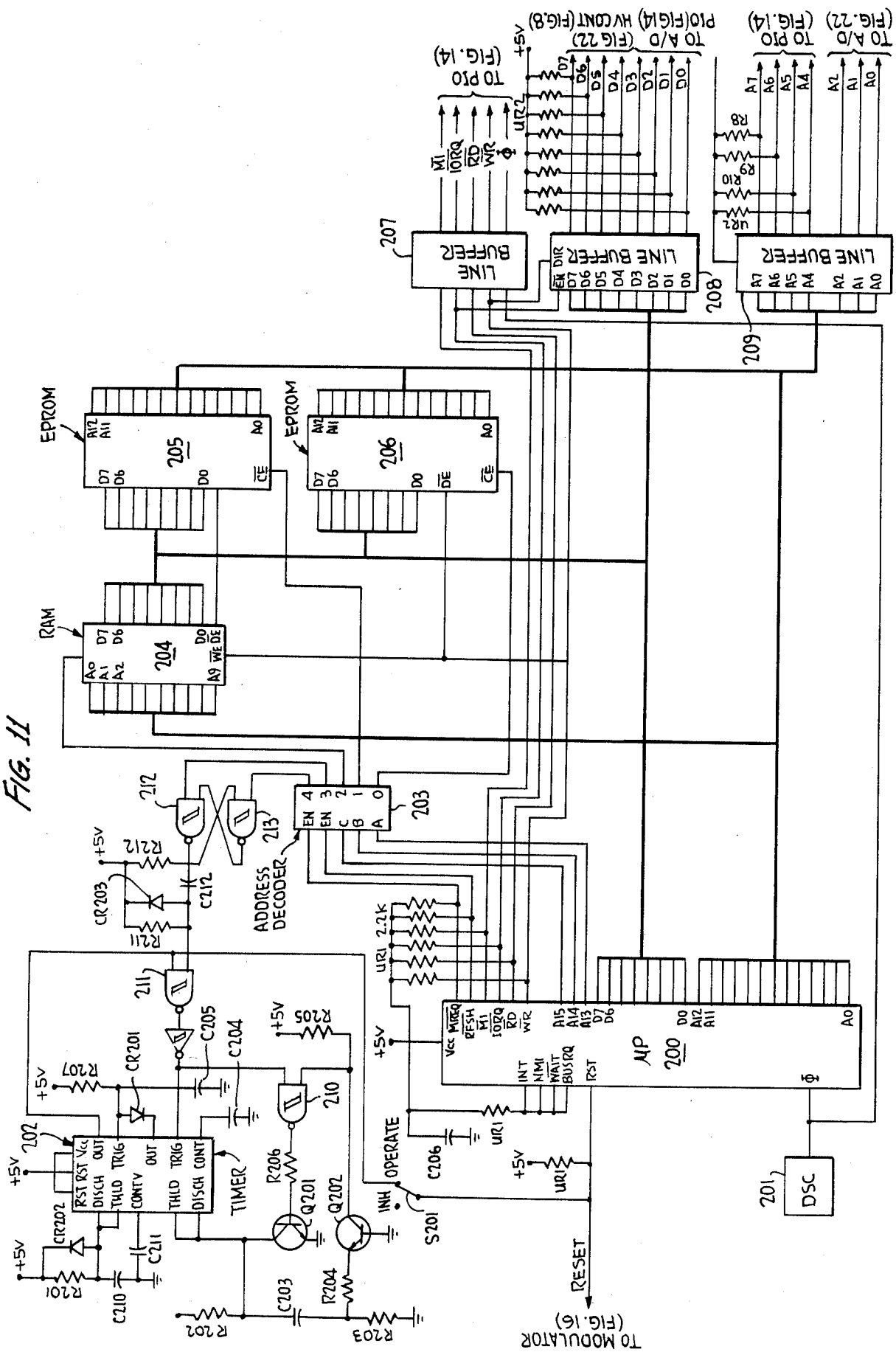
FIG. 11 is an electrical schematic diagram of the central processing unit employed in the present invention.

The CPU board circuit is illustrated in block diagram form in FIG. 10 and in detailed schematic form in FIG. 11. Specific reference is now made to these drawings.

The CPU board circuit includes a Z80 type microprocessor 200 (for example, Model MK 3880-4), a random access memory (RAM) 204 an erasable programmable read only memory (EPROM) 205 for data, and anotehr EPROM 206 for program instructions. RAM 204, for example, may be a Model MK 4118 AN-3. The EPROM's 205 and 206 may, for example, be Model type 2732A. The circuit also includes a reset timer 202, a clock 201, an address decoder or memory select circuit 203 and various line driver/buffer circuits 207, 208 and 209.

Microprocessor 200 is clocked at a four MHz rate by crystal-controlled oscillator 201. This clocking, in conjunction with other control signals, permits the circuit of FIG. 11 to control the various functions in the system by means of line buffer 207. The control signals provided through line buffer 207 are applied to the PIO circuit illustrated in FIG. 14 and described below.

The reset circuit for the microprocessor includes a timer 202, which is preferably part of a Model 556 dual timer integrated circuit. Timer 202 operates in conjunction with NAND gates 210, 211, 212 and 213 to generate a reset signal when the system power is turned on and to cause a system restart if the microprocessor should jump to an improper address or become caught in a continuous program loop. NAND gates 212 and 213 are connected in cross-coupled fashion to form a RS flip-flop. This flip-flop is toggled each time the correct sequence of addressing is initiated in the program for microprocessor 200. Output pulses from the flip-flop are applied to trigger the second section of timer 202. If the program fails to toggle the flip-flop (i.e., indicating improper program execution), capacitor C203 charges to the threshold required to trigger section 1 of timer 202 and thereby initiate a reset pulse through switch S201. Transistor Q201 serves as the discharge path for capacitor C203. Transistor Q202 is provided to assure full discharge of capacitor C203 by feeding the discharge pulse back to the base of transistor Q201. The time constant established by resistor R202 and capacitor C203 establishes the minimum time permitted between address pulses from the program before reset can occur. The time constant established by resistor R201 and capacitor C201 provides the time for the low level portion of the reset pulse. Resistor R207 and capacitor C205 establish the waiting period for initialization time after re-start. The reset inhibit switch S201 is utilized to disconnect the reset circuit from the microprocessor. This function is used for troubleshooting only and, if the reset function is disabled, the microprocessor must be reset manually.

RAM 204 is employed in conjunction with microprocessor 200 in a conventional manner for stack operations, scratch pad function, and power settings. Data used for outout power calculations are provided by EPROM 205. The program for microprocessor 200 is stored in EPROM 206. Address information to the PIO circuit (FIG. 14) and the A/D circuit (FIG. 22) is provided via line buffer 209. Line buffer 208 serves a similar function for the data bits D0–D7.

Figure 12:
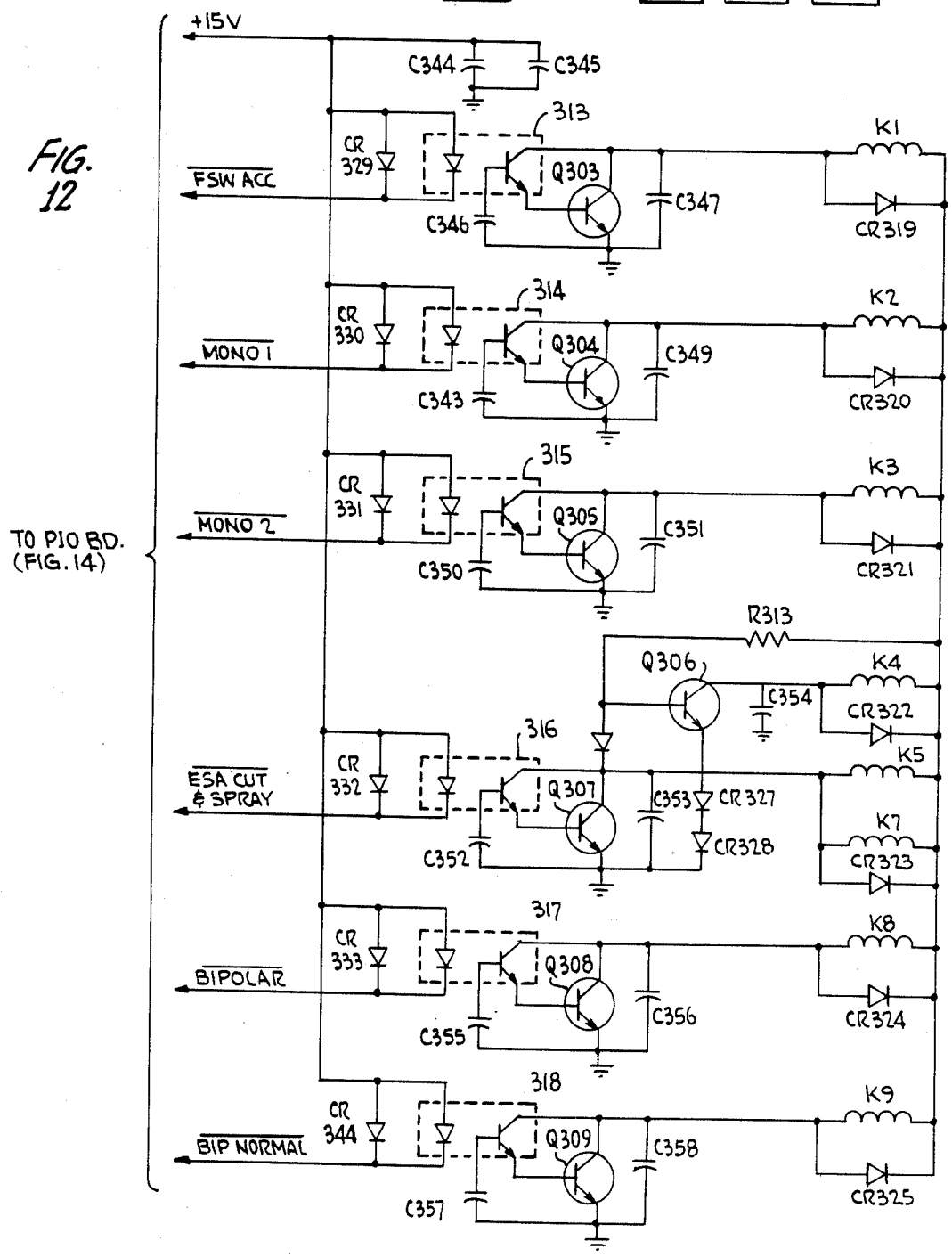
FIG. 12 is an electrical schematic diagram of one portion of the output board section employed in the electrosurgical generator of the present invention.
Figure 13:
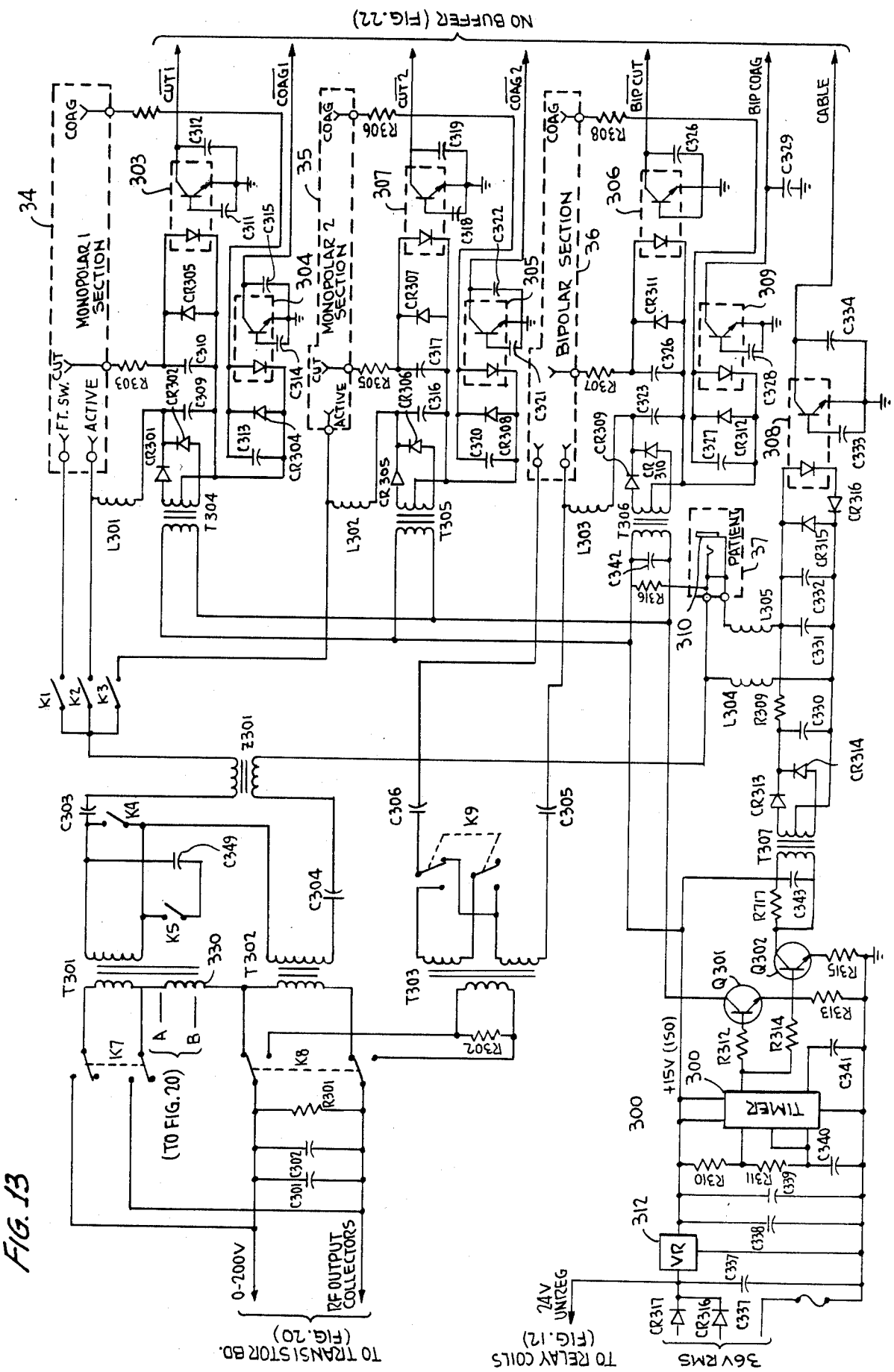
FIG. 13 is an electrical schematic diagram of another portion of the output board section employed in the electrosurgical generator of the present invention.

The output board assembly is illustrated in detail in FIGS. 12 and 13 of the accompanying drawings. Referring specifically to FIG. 12, relay commands from the PIO circuit of FIG. 14 are isolated from respective driver transistors for coils of relays K1–K5, K7–K9 by means of respective opto-isolators 313–318. The command signals are controlled by +15 volt logic whereas the relay coils are actuated by +24 volts. The coil for relay K1, which is connected across diode CR319, is actuated by the $\overline{\text{FSW ACC}}$ (foot switch accessory) signal which is applied to input side of opto-isolator 313 across diode CR329. The output transistor of opto-isolator 313 drives transistor Q303 to actuate the coil for relay K1. The coil for relay K2 is similarly driven by transistor Q304 which is actuated by opto-isolator 314 in response to the $\overline{\text{MONO 1}}$ signal. The coil for relay K3 is driven by transistor Q305, under the control of opto-isolator 315, in response to the $\overline{\text{MONO-2}}$ signal. In other words, relay coil K2 is energized when the monopolar-1 module is actuated; relay coil K3 is energized when the monopolar-2 module is actuated.

The ESA CUT & SPRAY signal actuates opto-isolator 316 to control transistor Q306 and transistor Q307. Transistor Q306 is used as a driver for the coil of relay K4; transistor Q307 is used as a driver for the coils of relays K5 and K7. Transistor Q307 is driven by the emitter circuit of the output transistor of opto-isolator 316; transistor Q306 is driven from the collector circuit of the output transistor of opto-isolator 316. Thus, transistor Q306 and transistor Q307 are never actuated at the same time; therefore, relay K4 is never energized at the same time as relays K5 and K7 which are always simultaneously energized. Relays K5 and K7 are energized during all of the spray and ESA CUT modes; relay K4 is energized in all of the COAG modes.

Relay K8 is energized by transistor Q307 by means of opto-isolator 317. Opto-isolator 317 is actuated in response to the $\overline{\text{BIPOLAR}}$ signal. Relay K9 is energized by means of the $\overline{\text{BIT NORMAL}}$ signal operating through opto-isolator 318 through transistor Q309.

The following table is a truth table showing the energization of the various relays for different accessory activation modes. An "X" in the column for the various relays indicates that the relay is energized for the corresponding accessory indicated in the row in which the "X" appears.

| RELAY TRUTH TABLE | | | | | | | |
|---|---|---|---|---|---|---|---|
| X = RELAY ENERGIZED | | | | | | | |
| ACCESSORY ACTIVATED | K1 | K2 | K3 | K4 | K5 | K7 | K8 | K9 |
| MONO 1, FOOTSWITCHED, CUT & COAG | X | | | X | | | | |
| MONO 1, FOOTSWITCHED, SPRAY | X | | | | X | X | | |
| MONO 1, HAND-SWITCHED, CUT & COAG | | X | | X | | | | |
| MONO 1, HAND-SWITCHED, SPRAY | | X | | | X | X | | |
| MONO 1, HAND OR FOOT-SWITCHED, ESA CUT | | X | | | X | X | | |
| MONO 1, HAND OR FOOT-SWITCHED, ESA COAG | | X | | X | | | | |
| MONO 2, HAND-SWITCHED, CUT & COAG | | | X | X | | | | |
| MONO 2, HAND-SWITCHED, SPRAY | | | X | | X | X | | |
| BIPOLAR, HAND OR FOOTSWITCHED, NORM | | | | | X | | X | X |
| BIPOLAR, HAND OR FOOTSWITCHED, WETF | | | | | X | | X | |

Referring specifically to FIG. 13, the various contacts K1–K9 correspond to relay contacts associated with the correspondingly designated relay coils K1–K5, K7–K9 in FIG. 12. The variable 200 V line and the RF OUTPUT line from the collectors of the output transistors at the transistor board circuit in FIG. 20 are connected to respective pairs of contacts in each of relays K7 and K8. These lines are also filtered by means of capacitors C301 and C302 and resistor R201 connected in parallel across the lines. The contacts for relay K8 directs the r-f energy for the cutting signals to either the monopolar transformer T302 or the bipolar transformer T303. When relay K8 is un-energized, contacts K8 are in the illustrated normally open position to connect the cutting signal to the primary winding of transformer T302. When relay K8 is energized, in response to the $\overline{\text{BIPOLAR}}$ signal (FIG. 12), the normally open contacts of relay K8 apply the r-f signal to the primary winding of transformer T303. Relay K7 is energized only during the spray or ESA cut functions. Unless these functions are activated, the r-f cutting signal is not applied to the primary winding of transformer T301. However, when relay K7 is energized, the cutting signal is applied to the primary winding of transformer T301. Relay K5 is always energized when relay K7 is energized so that high frequency filtering capacitor C349 is connected across the secondary winding of transformer T301 and the accessory circuitry when relay K7 is energized. The purpose of capacitor C349 is to short out high frequency harmonic components of the cutting signal through the transformer circuit.

Energization of relay K4 is complementary with energization of relay K7; therefore the contact for relay K4 does not provide a short circuit across the secondary winding of tranformer T301 when the primary winding is energized. The secondary winding of transformer T301 is connected in series through capacitor C303 and one side of a common mode transformer Z301 to each of contacts K1, K2 and K3. The other side of the secondary winding of transformer T301 is connected through the secondary winding of transformer T302, capacitor C304, and the other winding of common mode transformer Z301 to the patient cable jack 310. In other words, when relays K5 and K7 are energized, the primary windings of the spray or ESA transformer T301 and the monopolar transformer T302 are connected in parallel while the secondary windings of these transformers are connected in series.

Transformer T301 includes a feedback winding 330 for improving system operating stability in the open circuit condition. Specifically, feedback winding 330 provides negative feedback of the transformer signal to the driver circuit on the transistor board (FIG. 20).

Relay K9 is employed to select the normal 300-ohm or wetfield 50-ohm bipolar output impedance at the secondary windings of transformers T303. Relays K1, K2 and K3 have their contacts connected to direct the output signal from the monopolar transformer T302 to the appropriate monopolar accessory, namely monopolar-1 accessory 34 or monopolar-2 accessory 35.

The 36 volts rms voltage is rectified by diodes CR316 and CR317 to provide the +24 volts unregulated line used in the circuit of FIG. 12. This unregulated voltage is applied across capacitor C337 to voltage regulator 312 which, in conjunction with capacitor C338 and capacitor C339 provides a regulated +15 volts, isolated from ground, for utilization in the circuitry of FIG. 13. This isolated 15 volt supply is used as primary power for a timer 300 connected in conjuction with resistors R310, R311 and capacitors C340 and C341 to function as an oscillator having an output signal at 25 KHz. This output signal alternately switches transistors Q301 and Q302 through resistors R312 and R314 connected to the bases of these transistors, respectively. Transistor Q301 drives the primary windings for transformers T304, T305 and T306. Transistor Q302 drives the primary winding for transformer T307 and the patient cable continuity circuit. The secondary windings for each of transformers T304, T305, T306 and T307 provides an output signal which is rectified to produce 5 volts d.c. which is applied to the active lead of a corresponding accessory 34, 35, 36 and 37, respectively. Closing of an accessory switch connects isolated five volts from the ACTIVE jack to either the CUT or COAG jack. This actuates the corresponding opto-isolator 303, 304, 307, 305, 306, 309, or 308 to provide an appropriate signal to the microprocessor. These signals appear at the right-hand edge of the drawing in FIG. 13. Diodes CR305, CR304, CR307, CR308, CR311, CR312 and CR315 are connected in inverse parallel relation with the LED in respective opto-isolators 303, 304, 307, 305, 306, 309 and 308. These diodes serve to provide reverse breakdown protection for the high voltage r-f applied to the various accessories from the secondary windings of transformers T301, T302 and T303. When the patient cable is in good working order and is plugged into the patient jack 310, the cable provides a short circuit across the LED for opto-isolator 308 to turn that LED off. Inductors L304 and L305 provide high impedance to the r-f signal appearing at jack 310 so that only the isolated d.c. level is shorted across the LED for opto-isolator 308 by the patient cable.

It is noted that the monopolar-1 section 34 is substantially identical to the monopolar-2 section 35 except for the fact that section 34 includes the capability of foot-switch control. The contact for relay K1 provides r-f energy from the secondary winding of transformer T302 to the footswitch accessory jack. The contact for relay K2 is used to control application of the r-f signal to the ACTIVE jack of monopolar-1 section 34 for normal handswitch control. Similar application to the ACTIVE jack of monopolar-2 section 35 is provided through the contact for relay K3.

The PIO (peripheral input/output) circuit is illustrated in detail in FIG. 14 to which specific reference is now made. This circuit provides four eight-bit I/O ports using two I/O integrated circuits adapted for use with the Z80-type microprocessor. For example, each of the I/O circuits 350 and 351 may be a Model MK 3881 I/O integrated circuit. A four-to-sixteen line decoder 354 provides I/O port selection for the system. Decoder 354 may, for example, be a type 74LS154 decoder/demultiplexer.

The port B bits (PB0–PB7) of I/O circuit 350 are employed to control high voltage relays at the output board circuit in FIG. 12. As described above in relation to FIG. 12, these signals select the various output transformers and accessories.

Figure 16:
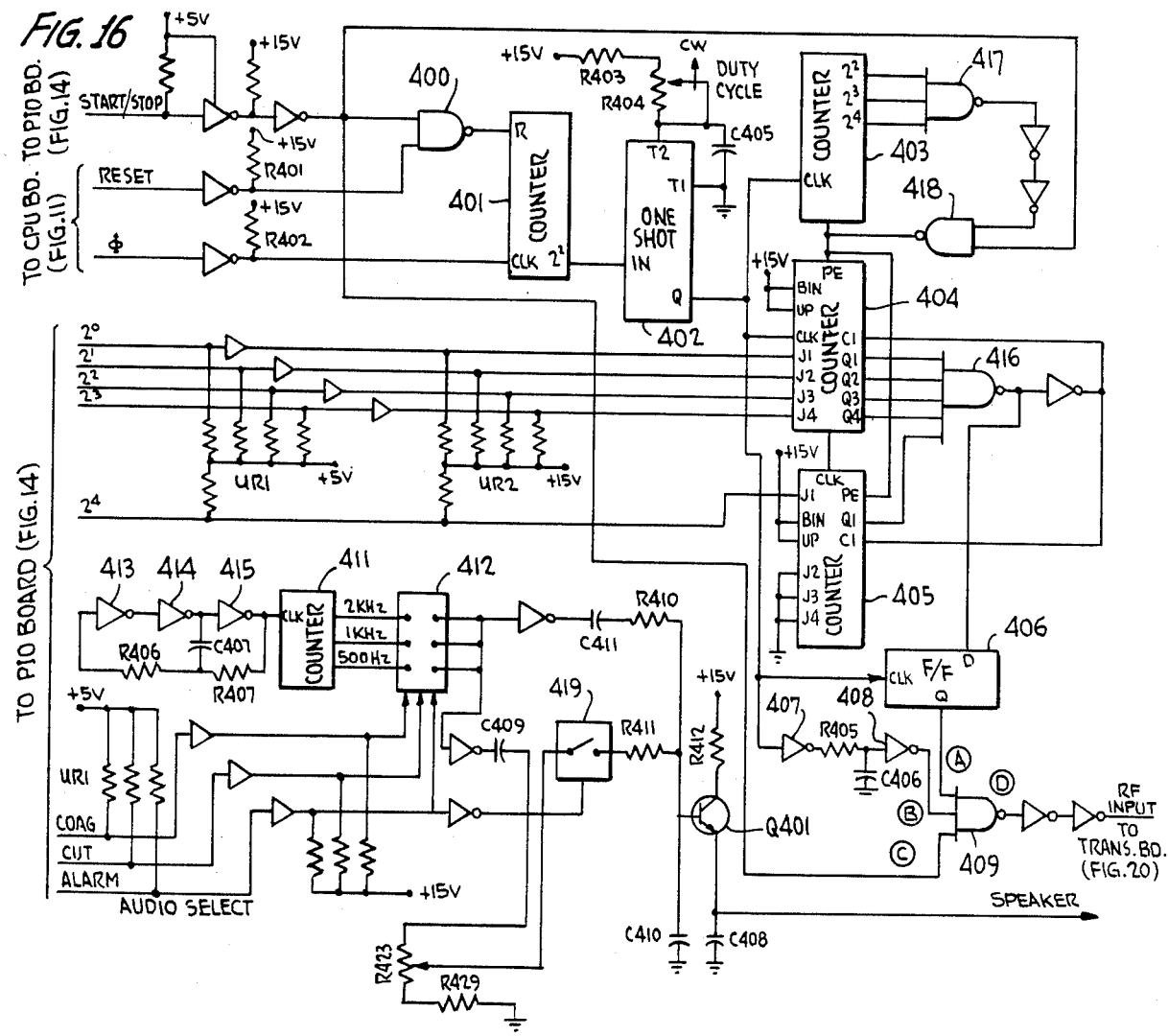
FIG. 16 is an electrical schematic diagram of the modulator circuit employed in the electrosurgical generator of the present invention.

The port A bits (PA0–PA7) of I/O circuit 351 control the modulator board (FIG. 16) pulse count as well as the start/stop r-f bits at the modulator board circuit. The CUT AUDIO and COAG AUDIO tones generated at the modulator board are also selected at port A of circuit 351. Port B of circuit 351 has mixed input and output functions. In particular, bit PB0 selects the audio alarm tone at the modulator board (FIG. 16). Bit PB1 monitors the a.c. line frequency. The square wave signal E (FIG. 9) generated in the high voltage control circuit (FIG. 8) is supplied for this bit as the LINE FREQ MON signal. The frequency of this square wave is determined under software control and a command is returned to the high voltage control board on the PB2 bit, designated LINE FREQ SEL to select 50 Hz or 60 Hz operation. The PB3 and PB4 bits provide CUT and COAG input footswitch signals. Bit PB6 controls the front panel service fault indicator lamp to indicate that a hardware fault has been detected. Bit PB7 is connected to the TEST contact of slide switch S401. In this position, the switch causes execution of a service program to begin at a power "ON" step. The second position of switch S401 is designated OPERATE and is the normal operating position of the switch. The service program is employed to calibrate the A/D converter at the A/D buffer circuit (FIG. 22).

The latches 352 for the data bits are employed in connection with dip switch 353 during system test.

The modulator circuit, designated by the reference numeral 14 in FIG. 1, is illustrated in detail in FIGS. 15, 16, and 18 of the accompanying drawings to which specific reference is now made. Reference is also made to FIG. 17 which is a timing diagram of various waveforms in the modulator circuit. The waveforms designated A-D in FIG. 17 appear at correspondingly designated points in the circuit of FIG. 16 as well as in the functional block diagram of FIG. 15. The 4 MHz clock from the microprocessor (FIG. 11) is applied to the CLK terminal of a counter 401 which divides the clock frequency by a factor of 8 to provide a 500 KHz signal to a one-shot multivibrator 402. The duty cycle of the output pulse bursts to be delivered to the transistor board (FIG. 20) is determined in accordance with the selected operated mode. The 500 KHz signal is the basis for the r-f cutting signal and is wave-shaped accordingly at the modulator board. The modulator board also contains all audio tone generators for providing audible indications of the operating mode.

The reset terminal of counter 401 receives the output signal from NAND gate 400, the input signals for which are derived from the START/STOP and RESET signals. These signals are generated to start and inhibit clocking of counter 401 under control of the microprocessor. The shaped 500 KHz pulses from one-shot 402 are applied to the CLK terminals of counters 403, 404 and flip-flop 406. Counter 403 sets the modulating frequency at 20 KHz by resetting itself through gates 417 and 418 after every twenty-five counts. Each thusly derived reset pulse for counter 403 is also applied to the preset enable terminals for counters 404 and 405. This has the effect of loading a five-bit number, provided from the PIO circuit (FIG. 14) into these counters. This five-bit pre-set number determines the number of pulses contained in each output burst of the r-f signal. When the five-bit counter formed by counters 404 and 405 reaches full count, NAND gate 416 sets the CI (Carry-In) terminals high at both counters to freeze the count therein until counter 403 is again reset. This action allows any number of pulses (from 0-25) to be programmed into a burst of the r-f cutting signal from the PIO board by the microprocessor.

The "D"-type flip-flop 406 functions to synchronize the modulation timing to the five hundred KHz clock signal. When the output signal from NAND gate 416 is driven low by a full count condition at the five-bit counter 404, 405, the falling edge of this output signal is not applied to NAND gate 409 (as signal A) until the next rising edge of the five hundred KHz clock signal (signal B) the programmed number of clock pulses are passed through NAND gate 409 during the time that the Q output signal of flip-flop 406 is held high. Of course, the start signal must be present, as signal C, at gate 409, in order for any clock pulses to pass through that gate. The resulting output signal D, which is supplied to the transistor board (FIG. 20) includes no clock pulses unless both of signals A and C are at high logic levels. The example of signal D illustrated in FIG. 17 is a "blend-3" mode signal wherein the r-f pulses are present for only forty percent of the time.

A four KHz oscillator, designated by the reference numeral 410 in FIG. 18, is made up of inverters 413, 414, 415, capacitor C407, and resistors R406 and R407 illustrated in FIG. 16. The resulting four KHz signal is applied to the CLK terminal of counter 411 which provides three distinct output pulse trains at two KHz, one KHz and five hundred KHz, respectively. These three signals constitute the alarm, cut and coag audio indicator tones, respectively. The appropriate tone is selected at switch 412 by the audio select signals COAG, CUT and ALARM received from the PIO circuit of FIG. 14. The cut and coag tones are applied to transistor amplifier Q401 through a volume control comprising adjustable resistor R403 and resistor R429. The alarm audio signal bypasses the volume control so that it cannot be turned down by the operator. In this regard, the alarm signal is passed through a separate switch 419 under the control of the audio select alarm control signal. The audio output signal from the circuit is connected across capacitor C408 to a speaker (not illustrated).

The transistor board circuitry, designated by reference numeral 16 in FIG. 1, is illustrated in detail in FIGS. 19 and 20 to which specific reference is now made. The transistor board contains the r-f power amplifiers, the high voltage power supply, the monitoring circuits and the transistor failure sensing circuitry.

The r-f power amplifier includes seven output transistors Q511, Q512, Q513, Q514, Q515, Q516 and Q517. The base and collector of each of these transistors are separately fused so that if one transistor fails, the generator continues to operate but at reduced power output capability. If a transistor fails, the collector fuse opens, thereby allowing a neon bulb at sensor 502 to fire. The associated phototransistor is rendered conductive when the neon bulb fires and provides a low logic level to the microprocessor via the A/D circuit in FIG. 22. The microprocessor senses the failed transistors only when the primary power is switched on.

A differential amplifier 506 is connected to monitor the high voltage level appearing on the 0-200 volt d.c. line and supplies the HV MON signal to the A/D buffer circuit (FIG. 22) for eventual monitoring by the microprocessor. A threshold for providing the HV MON signal is selected by means of variable resistor R534.

The r-f pulse train from the modulator board (FIG. 16) is capactively coupled by a capacitor C504 to the base of transistor Q501. When no r-f input signal is present, transistor Q501 is conductive and cuts off transistor Q502. The collector of transistor Q502 is supplied with voltage from a voltage regulator 501 which, in turn, receives the 24 volt unregulated supply voltage. Resistor R509 is adjustable to adjust the regulated output voltage from regulator 501 to a level which assures that transistor Q502 operates at a saturation level. Transistor Q502 drives the primary winding of transformer T501 to provide the current required to saturate the driver transistor Q508 connected to the secondary winding of the transformer. The base and collector of transistor Q508 are fused separately. A feedback network including resistor R512 and capacitor C506 connected in series, limits the high frequency gain of transistor Q508 to reduce unwanted oscillation and overshoot. Transistor Q508 drives the primary winding of transformer T502 to provide the high current pulses required to saturate the seven parallel-connected power transistors Q511-Q517. The negative feedback signal A-B from the feedback winding 330 of transformer T301 (FIG. 13) is connected across the high current pulse line in the secondary winding circuit of transformer T502 to provide improved system stability during open circuit operation.

Output power is controlled by varying the d.c. collector voltage for transistors Q511-Q517. The variable high voltage line (0-200 VDC) is controlled by the SCR full wave rectifier bridge BR501. Trigger signals for the two SCR's in bridge BR501 are applied to the gate electrodes of these SCR's through respective opto-isolators 503 and 504. The SCR gates are fired on alternate half-cycles of the 150 volt a.c. input signal which is derived from the same primary power line as is the ZERO CROSS AC signal utilized at the high voltage control circuit in FIG. 8 to derive the zero crossing detection pulses. Thus, the trigger signals derived in the high voltage control circuit trigger the SCR's at the selected times during the last one hundred degrees of each half-cycle, as described above. The full wave rectified, duty cycle-modulated output signal from bridge BR501 is applied to a smoothing pi-network filter including capacitors C512 and C520 and inductor L501 to provide the 0-200 volts d.c. (variable high voltage) bias for the power transistors. The high voltage is applied to the parallel collectors of transistors Q511-Q517 via the primary winding of the patient output transformer located at the output board described hereinabove in relation to FIG. 13. The A/D-buffer circuit, designated by the reference numeral 13 in FIG. 1, is illustrated in detail in FIGS. 21 and 22 to which specific reference is now made. This circuit includes an eight-channel analog-to-digital converter integrated circuit 602 which, by way of example, may be Model AD7581. The primary function of the circuit is to communicate handswitch information onto the data bus for the microprocessor.

The 4 MHz clock signal from the microprocessor is divided by four at frequency divider 600 to provide a 1 MHz signal at the CLK terminal of the A/D converter 602. In addition to this clock frequency, the A/D converter 602 requires a −10 volt reference which is provided by a voltage reference circuit 601 through an adjustable amplifier including operational amplifier 603 and adjustable resistor R604. Resistors R601 and R602 and capacitor C608 are associated with the voltage reference circuit 601. Resistors R603, R605 and R602 are associated with the variable resistor R604 in controlling the reference level. Amplifier 603 is employed to null the converter output voltage when no analog signal is being monitored.

Three input channels are utilized for high voltage supply monitoring, line voltage monitoring, and a gain reference signal for use with service test software. These channels are designated CH3, CH4 and CH0, respectively. Any input channel may be addressed by the microprocessor by means of address bits A0, A1 and A2, and the converted signal is placed on the output data bus applied to latch circuits 604.

There are six handswitch fault signals and one patient cable fault signal generated at the output board circuit (FIG. 13) and applied to the circuit of FIG. 22. These signals are filtered by respective RC circuits and applied through Schmitt trigger-type inverters which provide consistent switching thresholds for these signals. In addition, the inverters provide logic level shifting, from 15 volts to 5 volts, for data bus capability. A latch circuit 605 includes individual buffers for the fault signals, the buffers being enabled by the microprocessor via the PIO circuit to provide appropriate data on the data bus line (D0-D7). The eighth failure signal, namely the transistor failure signal, is derived from the transistor board (FIG. 20) and applied to latch 605 through opto-isolator 606.

Figure 24A:
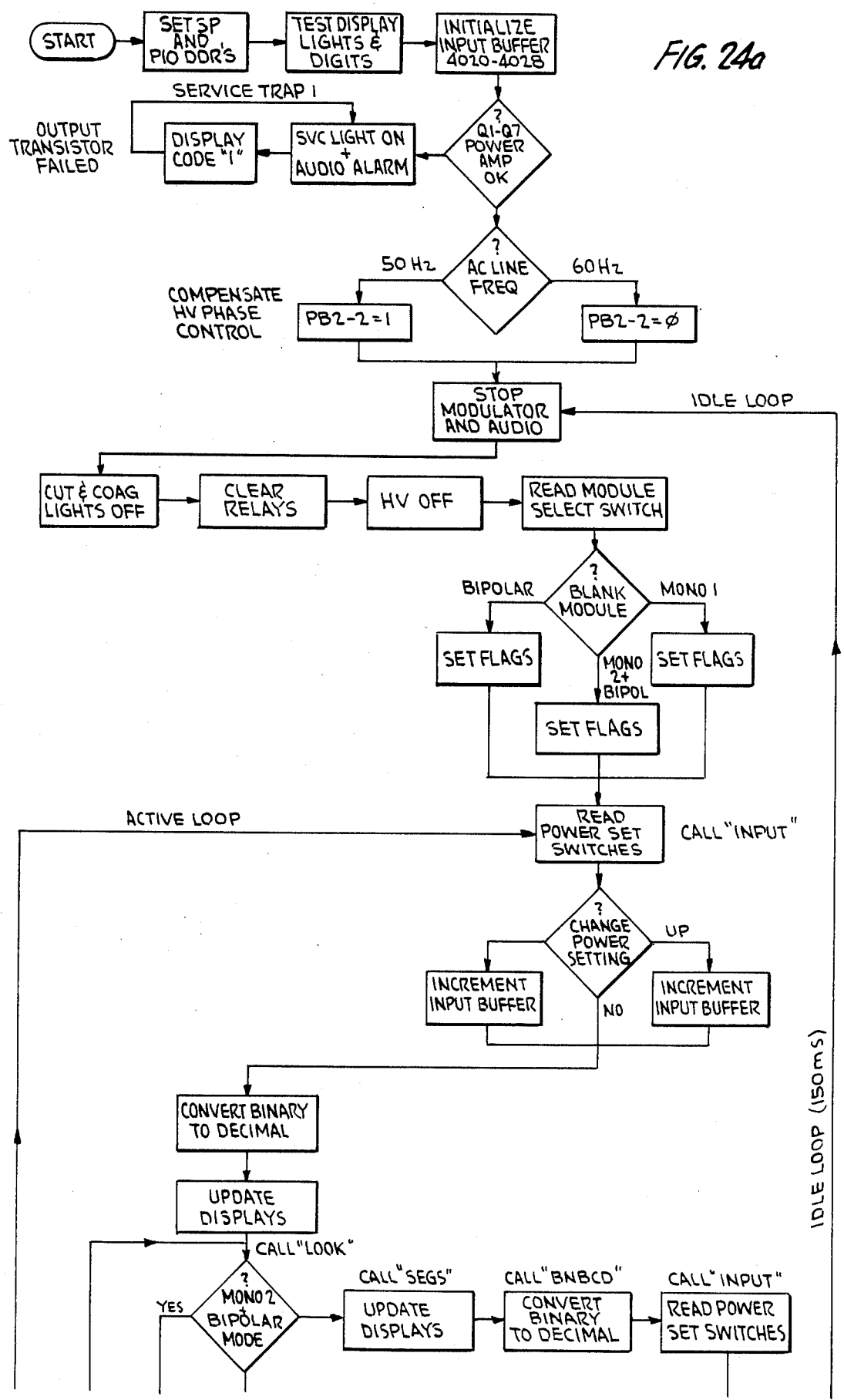
FIG. 24(a, b) is a flow chart of the software employed in the microprocessor utilized to control the operation of the electrosurgical generator of the present invention.

A flow chart for the software employed to control the microprocessor 200 is illustrated in FIGS. 24a and 24b. It is believed that the flow chart, when considered in conjunction with the description set forth above for the hardware, is sufficiently clear without further detailed discussion. The following brief description of system operation is provided, in conjunction with all of the drawings, to further explain the operation of the system.

The microprocessor circuitry illustrated in FIGS. 10 and 11 provides control signals for all of the system functions. Commands from the operator are applied from the controls in FIG. 23 and from the accessories connected at accessory jacks 34, 35, and 36, for use by the microprocessor. All input command switch positions are communicated directly to the microprocessor via the data bus (D0-D7) via the tri-state buffers 120, 121, 122 and 123 illustrated in FIG. 5.

The module select switch 21 (FIGS. 5 and 23) indicates to the microprocessor the identity of the modules 41, 42 and 43 from which to accept operator commands. Only those modules with lighted digital displays are active. When the power is turned on, all active modules are set to a zero watt power level. Thereafter, any change in position of the module select switch 21 results in a newly-activated module having its power set to zero. The digital displays DS1-DS16 indicate the predicted power to be delivered to a specific load resistance. The power level for all of the cut and coag modes, as described above, is set by the center "off" momentary contact rotary switches 24, 26, 28, 30, 31 and 32. When the microprocessor senses contact closure, it increments or decrements a memory location reserved for the corresponding control. This power control word is also stored in another memory location for subsequent comparison to detect memory error conditions. If an error is found, a software reset is initiated. The microproccessor increments the power by one watt each time the switch is turned. If the switch is held in a clockwise or counterclockwise position, the power increments slowly for up to 10 watts and then speeds up to reduce operator waiting time. The stored power control word is utilized to address a data table in data EPROM 205 in FIG. 12.

When the electrosurgical generator is idle and not providing an r-f output signal, the microprocessor monitors the patient cable, the handswitches, the footswitch, and front panel controls. When a handswitch or footswitch closure is detected, the following program sequence is initiated. First, a word is written into the PIO relay control port PB0-PB7 in I/O unit 350 of FIG. 14 to select an output transformer and the appropriate accessory models 41, 42 and 43. Next, the power control word for the activated mode is employed to recall a high voltage control word from the data tables in EPROM 205 of FIG. 11. This data word contains SCR phase control information which is written into data latch 159 of FIG. 8 at the high voltage control circuit. For example, if the TURP mode is selected, a thirty percent increase in power is calculated and employed for the first 300 milliseconds of the r-f power output. This thirty percent increase reduces the "drag" experienced during start up in an underwater cut. Thereafter, a word is written into the modulator and audio PIO control port PA0-PA7 at I/O unit 351 in FIG. 14. This word selects the audio tone and programs the wave shape to be generated in the cutting signal. A word is then written into the PIO light control port PA0-PA6 of I/O unit 350 in FIG. 14. A bit in this word turns on the cut and coag activation light at the front panel. Only one accessory and one mode may be activated at any time. All other switches are locked out until the presently activated mode is released.

When the monopolar-2 and bipolar modules are selected, the patient cable is not tested until the monopolar accessory is activated. This permits the "bipolar only" operation to ensue without connecting a dispersive pad. All output signals are isolated from ground and from one another to thereby permit a combination bipolar/monopolar servicing to be performed on a patient without removing the dispersive pad. When the generator is idle, all accessories are disconnected from the r-f amplifier by means of the relays K1–K9.

The following tables I–IX list, by way of example only, the values and/or model types for the various components illustrated in the drawings:

TABLE I

Power Supply Circuit (FIG. 3)

| Component - Value | Component Designation |
|---|---|
| Capacitor .01 mfd | C107–C113 |
| Capacitor 0.1 mfd | C116 |
| Capacitor 47 mfd | C115 |
| Capacitor 100 mfd | C114 |
| Capacitor 470 mfd | C104, C105, C106 |
| Capacitor 1000 mfd | C102, C103 |
| Capacitor 4700 mfd | C101 |
| Resistor 4.7 ohm | R113 |
| Resistor 39 ohm | R103, R105, R106, R108 |
| Resistor 100 ohm | R104, R107 |
| Resistor 120 ohm | R102 |
| Resistor 240 ohm | R109 |
| Resistor 270 ohm | R114 |
| Resistor 1K | R110 |
| Resistor 2.2K | R111, R112 |
| Potentiometer, 200 ohm | R101 |
| Diode, 1N4001 | CR104, CR106, CR107, CR108 |
| Diode, Suppressor 5 V | CR101 |
| Diode, Suppressor 15 V | CR102, CR103 |
| Diode, Zener 1N747A | CR105 |
| Triac, SC141B | Q101, Q102 |
| Transistor, PN2222A | Q103 |
| Transistor, MPSA13 | Q104 |
| Voltage Regulator, LM350K | 103 |
| Voltage Regulator, LM340K15 | 107 |
| Voltage Regulator, LM320T15 | 109 |
| Optoisolator IC, MOC634A | 114, 115 |
| AC Monitor IC, MID400 | 111 |

TABLE II

Display Circuit (FIGS. 5, 6)

| Component - Value | Component Designation |
|---|---|
| Resistor, 2.2K | All resistors |
| LED Driver IC, ICM 7218C | 124, 125 |
| Buffer IC, 74LS245 | 120–123 |
| Drivers, Transistor Array, ULN2803 | Lamp drivers |
| Indicator Lamp, 7572-W-14 | DS17–DS24 |

TABLE III

HV Control Circuit (FIG. 8)

| Component - Value | Component Designation |
|---|---|
| Capacitor .001 mfd | C157, C158 |
| Capacitor .01 mfd | C163, C164 |
| Resistor Network 10K | UR1 |
| Resistor 680 ohm | R172, R173 |
| Resistor 1K | R158, R161 |
| Resistor 1.2K | R157, R156 |
| Resistor 2.2K | R151–R153 |
| Resistor 10K | R159, R160, R163, R164, R170, R171 |
| Resistor 68K | R165 |
| Diode, 1N4001 | CR151 |
| Transistor, PN2222A | Q153–Q156 |
| 8 Bit Latch IC, 74LS373 | 159 |
| Buffer IC, 7407 | 180 |
| Oscillator IC, M1100 (277.65 KHZ) | 150 |
| Counter IC, 4526 | 151 |
| Inverter IC, 4049 | All Inverters |
| Nand Gate IC, 4012 | 153, 156 |
| Counter IC, 4029 | 154, 155, 157, 158 |

TABLE III-continued

HV Control Circuit (FIG. 8)

| Component - Value | Component Designation |
|---|---|
| Nand Gate IC, 4068 | 169, 170 |
| Nor Gate IC, 4078 | 160 |
| Nor Gate IC, 4001 | 161, 167, 168 |
| Nor Gate IC, 74LS02 | 171 |
| Comparator IC, LM393N | 162 |
| Exclusive-OR IC, 4070 | 163, 164, 178 |
| Timer IC, 556 | 165, 166 |

TABLE IV

CPU Circuit (FIG. 11)

| Component - Value | Component Designation |
|---|---|
| Resistor Network 2.2K | UR1, 2 |
| Resistor, 100 ohm | R204 |
| Resistor, 1K | R203 |
| Resistor, 2.2K | R208, R209, R210, R212 |
| Resistor, 4.7K | R206 |
| Resistor, 10K | R205, R211 |
| Resistor, 220K | R201, R207 |
| Resistor, 1 meg | R202 |
| Capacitor, .001 mfd | C212 |
| Capacitor, .01 mfd | C204, C211 |
| Capacitor, 0.1 mfd | C203, C205, C206, C210 |
| Diode, 1N4001 | CR201–CR203 |
| Transistor, PN2222A | Q201, Q202 |
| CPU IC, MK 3880N-4 | 200 |
| Decoder IC, 74LS138 | 203 |
| Oscillator IC, M1116-4 M | 201 |
| RAM IC, MK 4801AN-3 | 204 |
| EPROM IC, 2732A (data) | 205 |
| EPROM IC, 2764A (prog) | 206 |
| Buffer IC, 74LS244 | 207, 209 |
| Buffer IC, 74LS245 | 208 |
| Nand Gate IC, 74LS132 | 210–213 |
| Timer IC, 556 | 202 |

TABLE V

Output Circuit (FIGS. 12, 13)

| Component - Value | Component Designation |
|---|---|
| Capacitor 12000 pfd | C301, C302 |
| Capacitor .0047 mfd | C303 |
| Capacitor .001 mfd | C340 |
| Capacitor .01 mfd | C311, C314, C318, C321, C325, C328, C333, C341, C343, C346, C348, C350, C352, C355, C357 |
| Capacitor .01 mfd | C304–C306 |
| Capacitor 0.1 mfd | C332, C334, C339, C345, C347, C349, C351, C353, C354, C356, C358 |
| Capacitor 10 mfd | C309, C316, C323, C330, C344 |
| Capacitor 47 mfd | C338 |
| Capacitor 1000 mfd | C337 |
| Resistor 56 ohm | R313, R315 |
| Resistor 82 ohm | R309 |
| Resistor 120 ohm | R303–R308 |
| Resistor 6.8K | R310 |
| Resistor 10K | R312, R314 |
| Resistor 22K | R311, R318 |
| Resistor 220 ohm, ½ W | R316, R317 |
| Resistor 250 ohm, 20 W | R301, R302 |
| Diode, 1N4001 | CR301–CR334 |
| Transistor, 2N3019 | Q301, Q302 |
| Transistor, PN2222A | Q303–Q309 |
| Optoisolator IC, 4N38A | 303–309, 313–318 |
| Timer IC, 555 | 300 |
| Inductor, 33 uH | L301–L305 |

TABLE VI

PIO Circuit (FIG. 14)

| Component - Value | Component Designation |
|---|---|
| Capacitor 0.1 mfd | All Capacitors |
| Resistor Network 2.2K | UR1,2,3 |

TABLE VI-continued
PIO Circuit (FIG. 14)

| Component - Value | Component Designation |
|---|---|
| Resistor 270 ohm | R360 |
| Resistor 1K | R351-R358 |
| Resistor 4.7K | R359 |
| Transistor, PN2222A | Q351 |
| PIO IC, MK 3881N-4 | 350, 351 |
| Decoder IC, 74154 | 354 |
| Buffer IC, 7407 | All Inverters |
| Buffer IC, 74LS245 | 352 |

TABLE VII
Modulator Circuit (FIG. 16)

| Component - Value | Component Designation |
|---|---|
| Capacitor .001 mfd | C405, C406 |
| Capacitor .01 mfd | C407, C410 |
| Capacitor 1. mfd | C409, C411 |
| Capacitor 10 mfd, 35V | C408 |
| Resistor Network 2.2K | UR1 |
| Resistor Network 10K | UR2 |
| Resistor 47 ohm | R412 |
| Resistor 100 ohm | R405 |
| Resistor 680 ohm | R402 |
| Resistor 1.2K | R403 |
| Resistor 2.2K | R410, R411 |
| Resistor 10K | R401, R408, R409 |
| Resistor 12K | R406, R407 |
| Resistor, 4.7K | R429 |
| Potentiometer, 10K, multiturn | R423 |
| Potentiometer 1K, multiturn | R404 |
| Transistor, PN2222A | Q401 |
| Buffer IC, 7407 | All Inverters |
| Counter IC, 4029 | 404, 405 |
| Nand Gate IC, 4068 | 416 |
| Flip-Flop IC, 4013 | 406 |
| Nand Gate IC, 4023 | 417 |
| Counter IC, 4040 | 401, 403, 411 |
| Dual One Shot IC, 4528 | 402 |
| Analog Switch IC, 4066 | 412 |

TABLE VIII
Transistor Board Circuit (FIG. 20)

| Component - Value | Component Designation |
|---|---|
| Capacitor 100 pfd | C506 |
| Capacitor 1000 pfd | C507 |
| Capacitor 2200 pfd | C508 |
| Capacitor 4700 pfd | C505 |
| Capacitor .01 mfd | C510, C511 |
| Capacitor .1 mfd | C509 |
| Capacitor .1 mfd | C504, C513-C517 |
| Capacitor 1 mfd | C512 |
| Capacitor 10 mfd | C503 |
| Capacitor 47 mfd | C502 |
| Capacitor 100 mfd | C501 |
| Resistor 39 ohm | R526, R527 |
| Resistor 47 ohm | R505 |
| Resistor 100 ohm | R515, R516 |
| Resistor 240 ohm | R510 |
| Resistor 680 ohm | R508 |
| Resistor 1K | R502, R503 |
| Resistor 4.7K | R529 |
| Resistor 10K | R506 |
| Resistor 22K | R501 |
| Resistor 47K | R504 |
| Resistor 220K | R524 |
| Resistor 1 meg | R530-R533 |
| Resistor 10 ohm | R525 |
| Resistor 47 ohm | R512 |
| Resistor 100K | R535 |
| Resistor 5.1 ohm | R511 |
| Resistor 10 ohm | R507 |
| Resistor 0.5 ohm | R513, R517-R523 |
| Resistor 15K | R528 |
| Resistor 1K | R514 |
| Potentiometer 5K multiturn | R509 |
| Potentiometer 10K multiturn | R534 |

TABLE VIII-continued
Transistor Board Circuit (FIG. 20)

| Component - Value | Component Designation |
|---|---|
| Diode, 1N4001 | CR510, CR511 |
| Diode, 1N4005 | CR501-CR509 |
| Transistor, PN2222A | Q501, Q504 |
| Transistor, 2N6044 | Q502 |
| Phototransistor, MRD300 | Q503 |
| Voltage Regulator, LM317 | 501 |
| Opto Triac Driver IC, MOC 634A | 503, 505 |
| Op Amp IC, LM 324 | 506 |
| Neon Lamp, NE38/3 | DS1 in 502 |
| Inductor, 56mH | L512, L513 |
| Inductor, 820uH | L511 |

TABLE IX
A/D Circuit (FIG. 22)

| Component - Value | Component Designation |
|---|---|
| Capacitor .01 mfd | C608, C609, C620 |
| Capacitor 10 mfd, 35 V | C611 |
| Capacitor 0.1 mfd | All Other Capacitors |
| Resistor Network 2.2K | UR2 |
| Resistor Network 10K | UR1 |
| Resistor 1K | R602, R608, R609, R620 |
| Resistor 1.2K | R601 |
| Resistor 2.2K | R621 |
| Resistor 4.7K | R619 |
| Resistor 27K | R605, R617 |
| Resistor 56K | R603 |
| Resistor 150K | R606 |
| Resistor 10K | All Other Resistors |
| Potentiometer 1K | R607, R618 |
| Potentiometer 20K | R604 |
| Diode, suppressor, 12 V (SA12.A) | CR601 |
| Inverter IC, 4584 | U1 |
| Inverter IC, 4049 | U2 |
| Buffer IC, 74LS245 | 604, 605 |
| Opto-isolator IC, 4N38A | 606 |
| Flip-Flip IC, 74LS74 | 600 |
| Voltage Ref. IC, AD584 | 601 |
| Op-Amp IC, LM741 | 603 |
| A/D Converter IC, AD7581 | 602 |

The microprocessor-controlled electrosurgical generator of the present invention features dual independent handswitching output signals. This feature provides two surgeons with the capability of electrosurgery from a single unit while maintaining the capability of independent control over the respective required power output signals. Each surgical pencil has independent mode and power controls which are activated on a first-come/first-serve basis. All output signals are mutually isolated from one another and from ground to prevent accidental burns of the patient due to return path faults. The bipolar section provides two different waveforms with selective output impedance. The WET-FIELD mode is self-limiting with a 75-ohm impedance; the normal mode has a 300-ohm impedance. The bipolar output signal is isolated and independent from the monopolar section so that removal of the patient return pad is not necessary when the two modes are employed together.

The electrosurgical generator of the present invention includes two special procedure modes, namely: (1) the TURP mode (transurethral resection procedure) during which a "rapid start" power boost is provided for the first 300 milliseconds during demanding urological and reconstructive procedures; and (2) the ESA mode, designed for use in arthroscopic surgery where high impedance avascular tissues are encountered.

From the foregoing description it will be appreciated that the invention makes available a novel electrosurgical generator and a method for performing the electrosurgery wherein power output is accurately and precisely controlled, and wherein separate surgical pencils derive their power from the same electrosurgical generator at separately controlled power levels.

Having described a preferred embodiment of a new and improved electrosurgical generator constructed in accordance with the present invention, it is believed that other modifications, variations and changes will be suggested to those skilled in the art in view of the teachings set forth herein. It is therefore to be understood that all such variations, modifications and changes are believed to fall within the scope of the present invention as defined by the appended claims.

We claim:

1. An electrosurgical generator comprising:
    terminal means responsive to application of a cutting signal thereto for selectively delivering the cutting signal to a surgical site;
    signal generator means for providing a high frequency signal;
    adjustable gain amplifier means responsive to said high frequency signal for applying said high frequency signal to said terminal means as said cutting signal at an amplitude determined by the gain of said amplifier means; and
    gain control means for adjusting the gain of said amplifier means, said gain control means comprising:
        means for generating an alternating signal having a first predetermined frequency;
        control means for providing a control signal of variable duty cycle by inhibiting said alternating signal during a selected portion of each alternating signal cycle; and
        further means responsive to the duty cycle of said control signal for adjusting the gain of said amplifer means;
    wherein said control means comprises:
    a rectifier bridge for converting said alternating signal from a signal having successive half-cycles of alternating polarity to a signal having successive half-cycles with the same polarity, said rectifier bridge including first and second controlled rectifier means connected to conduct during opposite half-cycles of said alternating signal in response to respective applied first and second trigger signals;
    means for establishing a variable binary word; and
    trigger generator means for providing said first and second trigger signals at variable times during respective half-cycles of said alternating signal as a prescribed function of said established binary word.

2. The electrosurgical generator according to claim 1, wherein said trigger generator means comprises:
    means for inhibiting generation of said first and second trigger signals during a predetermined initial time interval at the start of each of said half-cycles; and
    further means for providing said first and second trigger signals at a time subsequent to said initial time interval during each said half-cycle, said time subsequent being directly related to the established binary word.

3. The electrosurgical generator according to claim 2 wherein said means for inhibiting comprises:
    first pulse generator means for providing a train of first inhibit pulses occuring at the start of positive half-cycles of said alternating signal, each first inhibit pulse having a duration which exceeds a half-cycle of said alternating signal by a time which is no greater than the predetermined initial time interval;
    second pulse generator means for providing a train of second inhibit pulses occuring at the start of negative half-cycles of said alternating signal, each second inhibit pulse having a duration which exceeds a half-cycle of said alternating signal by said time which is no greater than said predetermined initial time interval;
    first gating means connected to receive said first inhibit pulses for permitting passage of signals therethrough only in the absence of said first inhibit pulses; and
    second gating means connected to receive said second inhibit pulses for permitting passage of signals therethrough only in the absence of said second inhibit pulses; and
    wherein said further means comprises:
        means for generating clock pulses at a repetition frequency which is many times greater than said first predetermined frequency of said alternating signal;
        pre-settable binary counter means;
        means for pre-setting said counter means with said established binary word and initiating counting of said clock pulses by said counter means at the start of each half-cycle of said alternating signal;
        means responsive to a predetermined count accumulated in said counter means for generating a count pulse and terminating counting at said counter means for the remainder of the existing half-cycle of said alternating signal; and
        means for applying each count pulse to both said first and second gating means.

4. The electrosurgical generator according to claim 3 further comprising:
    switch means for individually activating a plurality of different cutting modes requiring respective different power levels of said cutting signal;
    wherein said means for establishing includes means for establishing said binary word in accordance with the cutting mode activated by said switch means.

5. The electrosurgical generator according to claim 4 further comprising manually adjustable means for permitting selective adjustment of the binary word established by said means for establishing.

6. The electrosurgical generator according to claim 4 wherein one of said cutting modes requires first and second different non-zero cutting signal power levels at first and second different times, respectively, during that one mode, and wherein said means for establishing includes means for providing a first binary word representing said first power level as the established binary word during said first time, and a second binary word representing said second power level as the established binary word during said second time.

7. The electrosurgical generator according to claim 3 wherein said terminal means comprises:
    a plurality of cutting pencils, each having its own actuation control; and
    means for selectively applying said cutting signal to said plurality of cutting pencils.

8. The electrosurgical generator according to claim 7 further comprising:

means responsive to actuation of each of said cutting pencils individually for applying said cutting signal to the actuated cutting pencil and inhibiting application of the cutting signal to subsequently actuated cutting pencils until the actuated cutting pencil is deactuated.

9. The electrosurgical generator according to claim 3 wherein the gain of said amplifier means is a function of the d.c. level of a bias signal; and wherein said further means comprises:
means for converting the control signal to a d.c. signal having an amplitude proportional to the control signal duty cycle; and means for applying said d.c. signal to said amplifier means as said bias signal.

10. The electrosurgical generator according to claim 3 wherein said high frequency is approximately an order of magnitude greater than said repetition frequency, and wherein said repetition frequency is an order of magnitude greater than the frequency of said alternating signal.

11. The electrosurgical generator according to claim 1 further comprising:
switch means for individually activating a plurality of different cutting modes requiring respective different power levels of said cutting signal, wherein said means for establishing includes means for establishing said binary word in accordance with the cutting mode activated by said switch means; and
manually adjustable means for permitting selective adjustment of the binary word established by said means for establishing.

12. The electrosurgical generator according to claim 1 wherein said terminal means comprises a plurality of cutting pencils, each having its own actuation control, and means for selectively applying said cutting signal to said plurality of cutting pencils, said generator further comprising:
means responsive to actuation of each of said cutting pencils, individually, for applying said cutting signal to the actuated cutting pencil and inhibiting application of the cutting signal to subsequently actuated cutting pencils until the actuated cutting pencil is deactuated.

13. The electrosurgical generator according to claim 12 wherein the gain of said amplifier means is a function of the d.c. level of a bias signal; and wherein said further means comprises:
means for converting the control signal to a d.c. signal having an amplitude proportional to the control signal duty cycle; and means for applying said d.c. signal to said amplifier means as said bias signal.

14. An electrosurgical generator comprising:
terminal means responsive to application of a cutting signal thereto for selectively delivering the cutting signal to a surgical site;
signal generator means for providing a high frequency signal;
adjustable gain amplifier means responsive to said high frequency signal for applying said high frequency signal to said terminal means as said cutting signal with a variable peak amplitude determined by the gain of said amplifier means; and
gain control means for adjusting the gain of said amplifier means, said gain control means comprising:
manually adjustable means for providing a selectively adjustable signal representing a desired power level of said cutting signal;
means for generating an alternating signal having a first predetermined frequency;
control means responsive to said selectively adjustable signal for providing a control signal of variable duty cycle by inhibiting said alternating signal during a selected portion of each alternating signal cycle as a function of said desired power level; and
further means responsive to the duty cycle of said control signal for adjusting the gain of said amplifier means to vary the peak amplitude of said cutting signal;
wherein the gain of said amplifier means is a function of a d.c. level of a bias signal; and
wherein said further means comprises:
means for converting the control signal to a d.c. signal having a d.c. level proportional to the control signal duty cycle; and means for applying said d.c. signal to said amplifier means as said bias signal.

15. The electrosurgical generator according to claim 14 wherein said terminal means comprises:
first and second accessory receptacle connectors for receiving in electrical contact first and second surgical pencils;
first and second mutually independent power adjustment controls for delivering adjustable electrical power to said first and second accessory receptacle connectors, respectively; and
first and second mutually independent operating mode selection control means for said first and second accessory receptacle connectors, respectively, to permit independent operating mode selection for each of said first and second pencils.

16. The electrosurgical generator according to claim 14 further comprising:
a transformer connected between said amplifier means and said terminal means and having a primary winding, a secondary winding and a feedback winding;
first switching means for alternatively connecting said primary winding to and disconnecting said primary winding from said amplifier means to alternatively apply and remove said cutting signal across said primary winding;
second switching means for controllable connecting said secondary winding to said terminal means; and
stabilizing means connecting said feedback winding between said signal generator means and said amplifier means in negative feedback relation.

17. The electrosurgical generator according to claim 14 wherein said manually adjustable means includes means for establishing a variable binary word as said selectively adjustable signal and wherein said control means comprises:
actuable gating means for alternatively passing and blocking said alternating signal; and
means responsive to the established binary word for actually said gating means at a variable actuation time during each cycle of said alternating signal, said actuation time being directly related to said established binary word.

18. The electrosurgical generator according to claim 17 further comprising:

switch means for individually activating a plurality of different cutting modes requiring respective different power levels of said cutting signal;

wherein said means for establishing includes means for establishing said binary word in accordance with the cutting mode activated by said switch means.

19. The electrosurgical generator according to claim 18 wherein said terminal means comprises:

a pluraltiy of cutting pencils, each having its own actuation control; and means for selectively applying said cutting signal to said plurality of cutting pencils.

20. The electrosurgical generator according to claim 19 further comprising:

means responsive to actuation of each of said cutting pencils individually for applying said cutting signal to the actuated cutting pencil and inhibiting application of the cutting signal to subsequently actuated cutting pencils until the actuated cutting pencil is deactuated.

* * * * *